(12) United States Patent
Chowdhury et al.

(10) Patent No.: US 9,527,893 B2
(45) Date of Patent: Dec. 27, 2016

(54) METHODS AND USES OF A MODIFIED CECROPIN FOR TREATING ENDOPARASITIC AND BACTERIAL INFECTIONS

(75) Inventors: Subrata Chowdhury, Charlottetown (CA); Michael Thomas Horne, Dunblane (GB)

(73) Assignee: SOLARVEST BIOENERGY INC., Montague, Prince Edward Island (CA)

( * ) Notice: Subject to any disclaimer, the term of this patent is extended or adjusted under 35 U.S.C. 154(b) by 0 days.

(21) Appl. No.: 14/232,488

(22) PCT Filed: Jul. 13, 2012

(86) PCT No.: PCT/CA2012/000662
§ 371 (c)(1),
(2), (4) Date: Jan. 13, 2014

(87) PCT Pub. No.: WO2013/006956
PCT Pub. Date: Jan. 17, 2013

(65) Prior Publication Data
US 2014/0170124 A1    Jun. 19, 2014

Related U.S. Application Data

(60) Provisional application No. 61/507,366, filed on Jul. 13, 2011.

(51) Int. Cl.
*A61K 39/00* (2006.01)
*C07K 14/435* (2006.01)
*A61K 38/00* (2006.01)

(52) U.S. Cl.
CPC ......... *C07K 14/43563* (2013.01); *A61K 38/00* (2013.01); *C07K 2319/00* (2013.01)

(58) Field of Classification Search
CPC ............................................. C07K 14/46563
See application file for complete search history.

(56) References Cited

U.S. PATENT DOCUMENTS

2007/0207209 A1*  9/2007  Murphy ................... A61K 9/06
                                                        424/484

\* cited by examiner

*Primary Examiner* — Albert Navarro

(57) ABSTRACT

The present disclosure provides a modified cecropin protein comprising a cecropin or a variant thereof fused to a hydrophilic tail lacking a C-terminal glycine. The present disclosure also provides pharmaceutical compositions, methods and uses of the modified cecropin protein or nucleic acid for treating or preventing endoparasites, such as *Plasmodium*, and bacteria.

20 Claims, 18 Drawing Sheets

SEQUENCE LISTING

<160> NUMBER OF SEQ ID NOS: 13

<210> SEQ ID NO 1
<211> LENGTH: 207
<212> TYPE: DNA
<213> ORGANISM: Artificial Sequence
<220> FEATURE:
<223> OTHER INFORMATION: Synthetic Construct

<400> SEQUENCE: 1

```
atgaacttta cgaagctgtt cattctggtg gcgatcgctg tgctggtgat cgccggcatc      60
cagccggccg atgctgcacc aaggtggaaa ttcggcaaac gacttgaaag gctgggtcgg     120
aatgtgttca aggcggccaa aaaagcactg ccagtcatcg ccgggtacaa ggccctcgga     180
gacccaaaag acgatgacgc taagtaa                                         207
```

<210> SEQ ID NO 2
<211> LENGTH: 68
<212> TYPE: PRT

<213> ORGANISM: Artificial Sequence
<220> FEATURE:
<223> OTHER INFORMATION: Synthetic Construct

<400> SEQUENCE: 2

```
Met Asn Phe Thr Lys Leu Phe Ile Leu Val Ala Ile Ala Val Leu Val
1               5                   10                  15

Ile Ala Gly Ile Gln Pro Ala Asp Ala Ala Pro Arg Trp Lys Phe Gly
            20                  25                  30

Lys Arg Leu Glu Arg Leu Gly Arg Asn Val Phe Lys Ala Ala Lys Lys
        35                  40                  45

Ala Leu Pro Val Ile Ala Gly Tyr Lys Ala Leu Gly Asp Pro Lys Asp
    50                  55                  60

Asp Asp Ala Lys
65
```

<210> SEQ ID NO 3
<211> LENGTH: 20
<212> TYPE: DNA
<213> ORGANISM: Artificial Sequence
<220> FEATURE:
<223> OTHER INFORMATION: Synthetic Construct

<400> SEQUENCE: 3
gtatccaacc tgccgatgct                                         20

<210> SEQ ID NO 4
<211> LENGTH: 22
<212> TYPE: DNA
<213> ORGANISM: Artificial Sequence
<220> FEATURE:
<223> OTHER INFORMATION: Synthetic Construct

<400> SEQUENCE: 4
gctagctcat tgtcgtcat cg                                       22

<210> SEQ ID NO 5
<211> LENGTH: 231
<212> TYPE: DNA
<213> ORGANISM: Artificial Sequence
<220> FEATURE:
<223> OTHER INFORMATION: Synthetic Construct

<400> SEQUENCE: 5
atgaacttta cgaagctgtt cattctggtg gcgatcgctg tgctggtgat cgccggcatc    60
cagccggccg atgctgcacc aaggtggaaa ttcggcaaac gacttgaaag gctgggtcgg    120
aatgtgttca aggcggccaa aaaagcactg ccagtcatcg ccgggtacaa ggccctcgga    180
gacccaaaag acgatgacgc taaggaccca aagacgatg acgctaagta a              231

<210> SEQ ID NO 6
<211> LENGTH: 76
<212> TYPE: PRT
<213> ORGANISM: Artificial Sequecne
<220> FEATURE:
<223> OTHER INFORMATION: Synthetic Construct

<400> SEQUENCE: 6

```
Met Asn Phe Thr Lys Leu Phe Ile Leu Val Ala Ile Ala Val Leu Val
1               5                   10                  15

Ile Ala Gly Ile Gln Pro Ala Asp Ala Ala Pro Arg Trp Lys Phe Gly
            20                  25                  30
```

```
Lys Arg Leu Glu Arg Leu Gly Arg Asn Val Phe Lys Ala Ala Lys Lys
             35                  40                  45

Ala Leu Pro Val Ile Ala Gly Tyr Lys Ala Leu Gly Asp Pro Lys Asp
     50                  55                  60

Asp Asp Ala Lys Asp Pro Lys Asp Asp Ala Lys
 65                  70                  75
```

<210> SEQ ID NO 7
<211> LENGTH: 255
<212> TYPE: DNA
<213> ORGANISM: Artificial Sequence
<220> FEATURE:
<223> OTHER INFORMATION: Synthetic Construct

<400> SEQUENCE: 7

```
atgaacttta cgaagctgtt cattctggtg gcgatcgctg tgctggtgat cgccggcatc     60
cagccggccg atgctgcacc aaggtggaaa ttcggcaaac gacttgaaag gctgggtcgg    120
aatgtgttca aggcggccaa aaaagcactg ccagtcatcg ccgggtacaa ggccctcgga    180
gacccaaaag acgatgacgc taaggaccca aaagacgatg acgctaagga cccaaaagac    240
gatgacgcta agtaa                                                     255
```

<210> SEQ ID NO 8
<211> LENGTH: 84
<212> TYPE: PRT
<213> ORGANISM: Artificial Sequence
<220> FEATURE:
<223> OTHER INFORMATION: Synthetic Construct

<400> SEQUENCE: 8

```
Met Asn Phe Thr Lys Leu Phe Ile Leu Val Ala Ile Ala Val Leu Val
 1               5                  10                  15

Ile Ala Gly Ile Gln Pro Ala Asp Ala Ala Pro Arg Trp Lys Phe Gly
             20                  25                  30

Lys Arg Leu Glu Arg Leu Gly Arg Asn Val Phe Lys Ala Ala Lys Lys
             35                  40                  45

Ala Leu Pro Val Ile Ala Gly Tyr Lys Ala Leu Gly Asp Pro Lys Asp
     50                  55                  60

Asp Asp Ala Lys Asp Pro Lys Asp Asp Ala Lys Asp Pro Lys Asp
 65                  70                  75                  80

Asp Asp Ala Lys
```

<210> SEQ ID NO 9
<211> LENGTH: 192
<212> TYPE: DNA
<213> ORGANISM: Artificial Sequence
<220> FEATURE:
<223> OTHER INFORMATION: Synthetic Construct

<400> SEQUENCE: 9

```
atgaacttta cgaagctgtt cattctggtg gcgatcgctg tgctggtgat cgccggcatc     60
cagccggccg atgctgcacc aaggtggaaa ttcggcaaac gacttgaaag gctgggtcgg    120
aatgtgttca aggcggccaa aaaagcactg ccagtcatcg ccgggtacaa ggccctcgga    180
gacccaaaat aa                                                        192
```

<210> SEQ ID NO 10
<211> LENGTH: 63
<212> TYPE: PRT
<213> ORGANISM: Artificial Sequence
<220> FEATURE:
<223> OTHER INFORMATION: Synthetic Construct

<400> SEQUENCE: 10

Met Asn Phe Thr Lys Leu Phe Ile Leu Val Ala Ile Ala Val Leu Val
1               5                   10                  15

Ile Ala Gly Ile Gln Pro Ala Asp Ala Ala Pro Arg Trp Lys Phe Gly
            20                  25                  30

Lys Arg Leu Glu Arg Leu Gly Arg Asn Val Phe Lys Ala Ala Lys Lys
        35                  40                  45

Ala Leu Pro Val Ile Ala Gly Tyr Lys Ala Leu Gly Asp Pro Lys
    50                  55                  60

<210> SEQ ID NO 11
<211> LENGTH: 279
<212> TYPE: DNA
<213> ORGANISM: Artificial Sequence
<220> FEATURE:
<223> OTHER INFORMATION: Synthetic Construct

<400> SEQUENCE: 11
atgaacttta cgaagctgtt cattctggtg gcgatcgctg tgctggtgat cgccggcatc      60
cagccggccg atgctgcacc aaggtggaaa ttcggcaaac gacttgaaag gctgggtcgg     120
aatgtgttca aggcggccaa aaaagcactg ccagtcatcg ccgggtacaa ggccctcgga     180
gacccaaaag acgatgacgc taaggaccca aaagacgatg acgctaagga cccaaaagac     240
gatgacgcta aggacccaaa agacgatgac gctaagtaa                           279

<210> SEQ ID NO 12
<211> LENGTH: 92
<212> TYPE: PRT
<213> ORGANISM: Artificial Sequence
<220> FEATURE:
<223> OTHER INFORMATION: Synthetic Construct

<400> SEQUENCE: 12

Met Asn Phe Thr Lys Leu Phe Ile Leu Val Ala Ile Ala Val Leu Val
1               5                   10                  15

Ile Ala Gly Ile Gln Pro Ala Asp Ala Ala Pro Arg Trp Lys Phe Gly
            20                  25                  30

Lys Arg Leu Glu Arg Leu Gly Arg Asn Val Phe Lys Ala Ala Lys Lys
        35                  40                  45

Ala Leu Pro Val Ile Ala Gly Tyr Lys Ala Leu Gly Asp Pro Lys Asp
    50                  55                  60

Asp Asp Ala Lys Asp Pro Lys Asp Asp Asp Ala Lys Asp Pro Lys Asp
65                  70                  75                  80

Asp Asp Ala Lys Asp Pro Lys Asp Asp Ala Lys
            85                  90

<210> SEQ ID NO 13
<211> LENGTH: 60
<212> TYPE: PRT
<213> ORGANISM: Anopheles darlingi

<400> SEQUENCE: 13

Met Asn Phe Thr Lys Leu Phe Ile Leu Val Ala Ile Ala Val Leu Val
1               5                   10                  15

Ile Ala Gly Ile Gln Pro Ala Asp Ala Ala Pro Arg Trp Lys Phe Gly
            20                  25                  30

-continued

```
Lys Arg Leu Glu Arg Leu Gly Arg Asn Val Phe Lys Ala Ala Lys Lys
        35                  40                  45

Ala Leu Pro Val Ile Ala Gly Tyr Lys Ala Leu Gly
    50                  55                  60
```

METHODS AND USES OF A MODIFIED CECROPIN FOR TREATING ENDOPARASITIC AND BACTERIAL INFECTIONS

RELATED APPLICATIONS

This application is a national stage entry under 35 USC §371(b) of International Application No. PCT/CA2012/000662, filed Jul. 13, 2012, and claims priority under 35 U.S.C. §119 to U.S. Provisional Application Ser. No. 61/507,366 which was filed on Jul. 13, 2011, the entirety of both of which are incorporated herein by reference.

INCORPORATION BY REFERENCE OF MATERIAL SUBMITTED ELECTRONICALLY

Incorporated by reference in its entirety is a computer-readable sequence listing identified as follows: one 7,439 byte ASCII (text) file named "PCTCA2012000662-seq1-000001-EN-20120726.txt", created on Jan. 13, 2014.

FIELD

The present disclosure relates to a modified cecropin anti-microbial peptide and methods and uses thereof for inhibiting endoparasites or bacteria and for use in treating or preventing endoparasitic or bacterial infections.

BACKGROUND

Malaria is a mosquito-borne disease and, despite many years of research, remains a major global health problem causing illness and death that disproportionately affects developing countries. The worldwide incidence of malaria is estimated by the World Health Organization to be approximately 300 to 500 million clinical cases annually, with at least one million deaths. The majority of these are young children [WHO Malaria report 2008, Snow et al. 2005, Guerra et al. 2008 and Hay Si et al. 2009]. The emergence of insecticide-resistant mosquito vectors and multi-drug resistant parasites has contributed to resurgences of the disease.

A number of anti-malarial vaccines has been used to combat the disease with some ameliorative effects [Bejon P. et al., 2009] and new vaccines and treatments regularly appear on the market. The determination of efficacy from these is difficult and compounded by the generally poor health status of many of the trial groups. To date, none has appeared to be highly protective but any vaccine that reduces morbidity and mortality is a valuable new tool in the fight against malaria. The most severe form of the disease is caused by Plasmodium falciparum [Casteels, P. C. et al. 1989, Chopra, L. 1993]. Infection begins when malarial sporozoites are injected by mosquitoes into the host and within minutes parasites invade hepatocytes, where they multiply and differentiate into the next stage of the life-cycle, the merozoites. The merozoites emerging from the hepatocytes invade red blood cells leading to clinical illness [Sturm A. et al. 2006]. The most advanced vaccine candidate, designated RTS, S/AS02A, [Bejon P. et al. 2009] is based on the major sporozoite surface antigen. However, this candidate vaccine, currently in Phase 3 clinical trials, has shown only 30-65% efficacy in field studies [Dauville D. et al. 2010] and a vaccine with higher levels of protection is still sought. Over a period of time, people living in areas where malaria is endemic develop immunity to clinical disease caused by P. falciparum and immunoglobulin G taken from immune adults has been shown to reduce parasite density and clinical symptoms when administered to children with clinical malaria [Cohen et al. 1961, Bauharoun-Tayoun H. et al. 1990, Sabchareon A. et al. 1991]. Thus, proteins expressed during the blood-stage of the life cycle are good candidates for inclusion in a vaccine [Good M. F. 2001. Malkin E. at al. 2007], as a blood-stage vaccine would reduce or prevent severe illness and complications of the disease.

Many microbial pathogens, viral or bacterial, include a secondary host in their life-cycle which in many cases shows no overt signs of disease in contrast to that of the host with which the disease is primarily associated. The secondary host in these cases provides an environment which is physiologically permissive for growth and differentiation of the pathogen, frequently without any detrimental effect to itself. In the mosquito, malarial association however, where the mosquito acts as an efficient vector for transmission of the Plasmodium parasite to mammals, the mosquito nevertheless presents multiple barriers to the unrestricted growth of the parasite minimising multiplication in this part of the life-cycle [Warburg and Miller, 1991; Beier, 1998]. These barriers arise from a number of factors, including anatomical features of the mosquito host and physiological incompatibilities between insect and parasite.

It is probable that the innate immune system of the mosquito plays a significant part in this restriction of parasite growth or development and may be the predominant source of this controlling effect. Insects in general respond to bacterial or fungal infections by rapidly synthesizing a battery of potent antimicrobial peptide factors [Hetru et al., 1998]. The cloning of genes encoding these peptides in model insect species, particularly the fruit fly Drosophila melanogaster, has provided powerful tools with which to explore the mechanisms involved in the elicitation of the insect innate immune response [Hoffmann et al. 1996]. Recently, progress has been made in applying this basic knowledge of invertebrate immunity to dipteran insects of medical importance [Richman & Kafatos, 1996]. In particular, interest has focused on the mosquito Anopheles gambiae which is the most important african vector of the human malaria parasite Plasmodium falciparum and on Aedes aegypti the transmitter of yellow fever. This species is also a vector of a number of other protozoan and metazoan parasites. Initial studies of humoral immunity in both of these insect species has led to the purification of a group of antimicrobial peptides known as "defensins" and to the cloning of defensin-encoding cDNAs [Chalk et al. 1994; Lowenberger et al. 1995; Cho et al. 1996; Richman and Kafatos, 1996]. Both A. gambiae and A. aegypti respond to bacterial infections through the rapid induction of defensin RNA and protein [Lowenberger et al. 1995; Richman et al. 1996].

Further studies in A. gambiae have shown that humoral immune mechanisms are activated in multiple host mosquito tissues and at multiple time points during the course of infection of the mosquito by the rodent malarial parasite, Plasmodium berghei [Richman et al. 1997; Dimopoulos et al. 1998]. The fact that immune-competent mosquitoes nevertheless provide a physiological milieu at least partially permissive for the growth and differentiation of Plasmodium, represents an intriguing biological phenomenon of great significance for human health.

The extent to which endogenous humoral effector molecules may act to limit parasite development or growth in insects is largely unknown. Defensins have been shown to have effects on certain stages of *Plasmodium* either in vitro or when injected into the haemolymph of infected mosquitoes [Shahabuddin et al. 1998]. However, a microorganism or parasite invading a dipteran insect will probably encounter multiple humoral defense factors which may act synergistically.

Calvo et al. (2009) isolated an anti-microbial peptide, a cecropin homologue, from the salivary gland of the mosquito *A. darlingi*. Cecropins are powerful antimicrobial compounds present in insect haemolymph and are also found in pig intestines [Boman, H. G. 1991; Boman, H. G., et al. 1991; Lee, J. Y., et al. 1989]. They are strongly cationic, amphipathic, α-helical peptides with 35 to 39 residues and are notably active not only against certain gram-positive bacteria but also against gram-negative bacteria. Many other cationic peptides, such as defensins from leukocyte granules and magainins from frog skin, have also evoked considerable interest in recent years [Casteels, P. C. et al. 1989; Diamond, G., et al. 1991; Lehrer, R I., et al. 1991; Nakamura, T. et al. 1988; Parra-Lopez, C., 1993; Zaslof, M. 1987; Zasloff, M., B. et al. 1988]. However, cecropins are 10 to 30 times more active than defensins and magainins, against *Escherichia coli* and *Pseudomonas aeruginosa* [Boman, H. G. 1991; Wade, D. A. et al. 1990].

The strongly cationic N-terminal, amphipathic helix of cecropins has been shown to be necessary for effective binding to bacterial membranes allowing them to cause instantaneous lysis of bacterial cells, through disintegration of the cytoplasmic membrane [Christensen, B. J. 1988]. Cecropins form ion channels in artificial membranes [Christensen, B. J. et al. 1988], and cecropin dimers can be predicted by computer modeling to form channel-containing regular lattice structures on the membrane surface [Durell, S. R., et al. 1992]. However, such channels probably develop only when the cecropin density is high and disintegration of the membrane takes place [Christensen, B. J. et al. 1988; Durell, S. R., et al. 1992]. Accordingly, the lethal target of cecropins in these studies was the bacterial cytoplasmic membrane.

Cecropin molecules possess amphipathicity which allows them to interact simultaneously with lipid-like and negatively charged molecules through their cationic region, so as to attach themselves to the microbial membrane (Ganz T, and Lehrer R I, 1998). The initial contact between the peptide and the target organism is electrostatic. Their amino acid composition, amphipathicity, cationic charge and size allow them to insert into the membrane bilayer to form pores by attaching themselves as a 'carpet' to penetrate the membrane (Giuliani et al., 2007).

With the exception of *Bombyx* and *Aedes* cecropins, all other insect cecropins so far characterized are C-terminally amidated. This post-translational modification has been considered necessary for the full anti-microbial activity of the molecule (Li et al. 1988; Hara et al. 1994), and may protect the peptide from carboxypeptidase digestion (Callaway et al. 1993). The presence of a glycine residue at the end of the deduced amino acid sequence of *A. Gambiae* cecropin suggested C-terminal amidation via terminal glycine removal (Bradbury & Smyth, 1991) produced a fully active peptide.

SUMMARY

The present inventors have modified the anti-microbial peptide, cecropin, to provide both stability and increased activity against endoparasites and bacteria.

Accordingly, the present disclosure provides a cecropin or variant thereof fused to a hydrophilic tail lacking a C-terminal glycine. In one embodiment, the hydrophilic tail comprises 3 to 24 amino acids, optionally 8-16 amino acids, optionally 3, 8, 16 or 24 amino acids. In one embodiment, the modified cecropin comprises the amino acid sequence as shown in SEQ ID NO:2 or a variant thereof. In another embodiment, the modified cecropin comprises the amino acid sequence as shown in SEQ ID NO:6 or a variant thereof. In yet another embodiment, the modified cecropin comprises the amino acid sequence as shown in SEQ ID NO:8 or a variant thereof. In a further embodiment, the modified cecropin comprises the amino acid sequence as shown in SEQ ID NO:10 or a variant thereof.

In another embodiment, the present disclosure provides a nucleic acid molecule encoding the modified cecropin disclosed herein. In one embodiment, the nucleic acid encodes a modified cecropin having the amino acid sequence as shown in SEQ ID NOs:2, 6, 8 or 10 or a variant thereof or having the nucleic acid sequence as shown in SEQ ID NOs:1, 5, 7 or 9 or a variant thereof. Also included is a vector comprising the nucleic acid molecule disclosed herein. Further provided is a host cell comprising the vector disclosed herein. In one embodiment, the host cell is a yeast cell.

In yet another embodiment, the present disclosure provides a pharmaceutical composition comprising a modified cecropin disclosed herein, a nucleic acid molecule disclosed herein, a vector disclosed herein or a host cell disclosed herein, and a pharmaceutically acceptable carrier.

In a further embodiment, the present disclosure provides a method of inhibiting endoparasites or bacteria comprising administering a modified cecropin disclosed herein, a nucleic acid disclosed herein, a vector disclosed herein or a host cell disclosed herein to an animal in need thereof. Also provided herein is a use of a modified cecropin disclosed herein, a nucleic acid disclosed herein, a vector disclosed herein or a host cell disclosed herein for inhibiting endoparasites or bacteria in an animal in need thereof. Further provided herein is a use of a modified cecropin disclosed herein, a nucleic acid disclosed herein, a vector disclosed herein or a host cell disclosed herein in the preparation of a medicament for inhibiting endoparasites or bacteria in an animal in need thereof. Even further provided herein is a modified cecropin disclosed herein, a nucleic acid disclosed herein, a vector disclosed herein or a host cell disclosed herein for use in inhibiting endoparasites or bacteria in an animal in need thereof.

In a further embodiment, the present disclosure provides a method of treating or preventing an endoparasitic or bacterial infection comprising administering a modified cecropin disclosed herein, a nucleic acid disclosed herein, a vector disclosed herein or a host cell disclosed herein to an animal in need thereof. Also provided herein is a use of a modified cecropin disclosed herein, a nucleic acid disclosed herein, a vector disclosed herein or a host cell disclosed herein for treating or preventing an endoparasitic or bacterial infection in an animal in need thereof. Further provided herein is a use of a modified cecropin disclosed herein, a nucleic acid disclosed herein, a vector disclosed herein or a host cell disclosed herein in the preparation of a medicament for treating or preventing an endoparasitic or bacterial infection in an animal in need thereof. Even further provided herein is a modified cecropin disclosed herein, a nucleic acid disclosed herein, a vector disclosed herein or a host cell disclosed herein for use in treating or preventing an endoparasitic or bacterial infection in an animal in need thereof. In one embodiment, the endoparasitic infection is malaria. In another embodiment, the bacterial infection is an *E. coli* or *Pseudomonas* infection.

In one embodiment, a modified cecropin disclosed herein, a nucleic acid disclosed herein, a vector disclosed herein or a host cell disclosed herein is administered or used orally.

Other features and advantages of the present disclosure will become apparent from the following detailed description. It should be understood, however, that the detailed description and the specific examples while indicating embodiments of the disclosure are given by way of illustration only, since various changes and modifications within the spirit and scope of the disclosure will become apparent to those skilled in the art from this detailed description.

BRIEF DESCRIPTION OF THE DRAWINGS

The disclosure will now be described in relation to the drawings in which.

DETAILED DESCRIPTION

Figure 1:
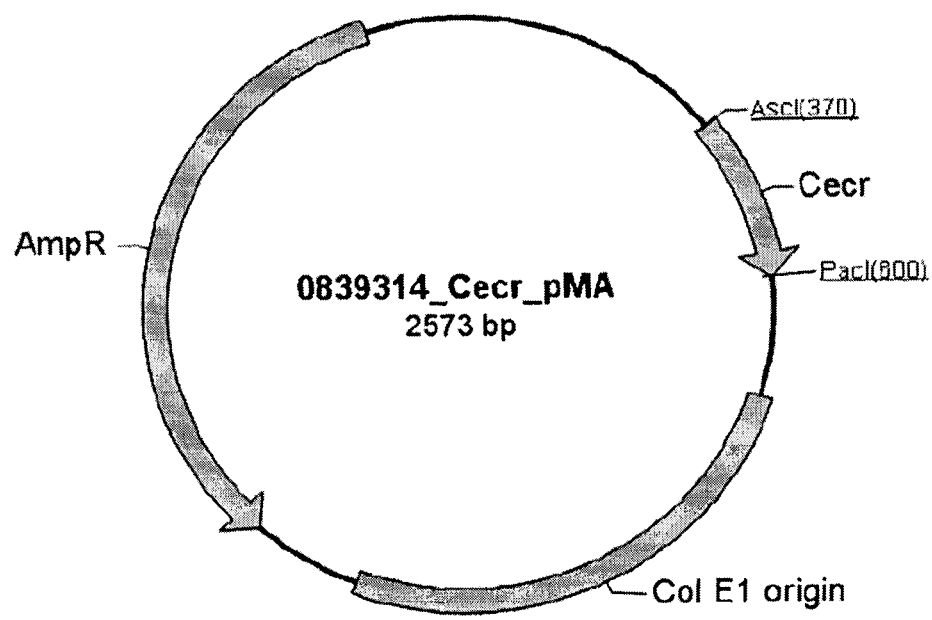
FIG. 1 shows a plasmid map of 0839314_Cecr_pMA.
Figure 2:
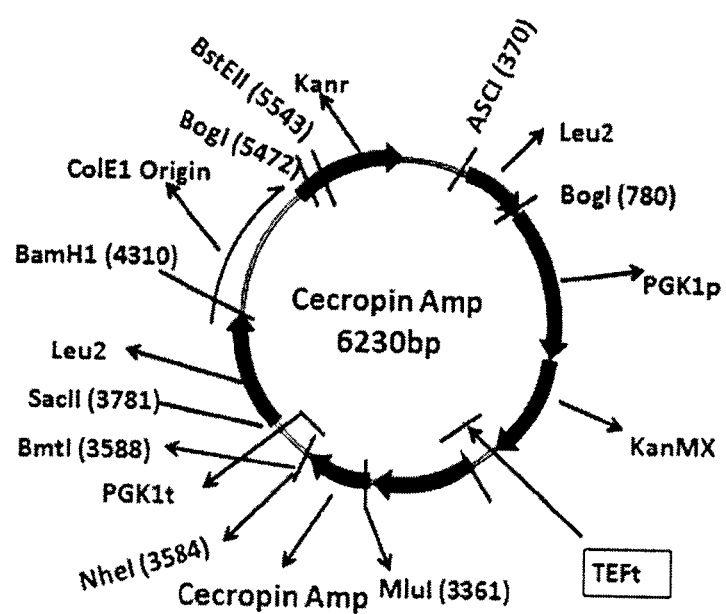
FIG. 2 shows the structure of the plasmid used to transform the modified cecropin gene into yeast.

The present inventors have engineered a modified cecropin protein which has an added hydrophilic tail fused to the C-terminal glycine residue of cecropin. The resulting modified protein does not have a glycine at the C-terminal end allowing the peptide to avoid amidation by enzymes when administered. If the peptide is amidated, it becomes very stable to the extent that it is predicted to induce antibody in the host and any drug made from such a peptide would be ineffective. The addition of a hydrophilic tail to the C-terminal glycine keeps the peptide out of carboxypeptidase digestion, i.e. provides enough stability (Khmelnitsky et al. 1991) so that the peptide does not disappear prior to exerting its effect on the endoparasite or bacterium. The tail also provides improved electrostatic binding of cecropin to the endoparasite or bacterium. The modified cecropin, which has both stability and improved binding, is useful in treating or preventing endoparasitic infections, such as malaria and bacterial infections.

The definitions disclosed herein are applicable throughout the disclosure even if a definition is only found in one section.

Proteins and Nucleic Acids

The present disclosure provides a modified cecropin protein comprising a cecropin or a variant thereof fused to a hydrophilic tail lacking a C-terminal glycine.

The term "cecropin" as used herein is intended to refer to the anti-microbial peptide cecropin from any species, form or source and typically ranges in size from 35 to 39 amino acids. The term "cecropin nucleic acid" is intended to encompass a nucleic acid encoding a cecropin anti-microbial peptide. The DNA, mRNA and protein sequences of cecropin A [*Drosophila melanogaster*] are found in GeneBank AAF57025.1. The DNA, mRNA and protein sequences of cecropin B [*Drosophila melanogaster*] are found in GenBank: AAF57027.1 from *Anopheles darlingi*, NCBI accession number AD-57-208657655 (SEQ ID NO:13), and Gene Bank accession number is ACI30167. The DNA, mRNA and protein sequence of Cecropin C from *Drosophila melanogaster* Gene Bank accession number is AAF 57028. The DNA, mRNA and Protein sequence of Cecropin D from *Bombyx mori* are found in GenBank BAA31507.1.

The cecropin family of proteins is related structurally but varies in efficiency of binding and lysing various target endoparasites and bacteria. *Plasmodium falciparum* and *Trypanosoma cruzi* were killed by two novel lytic peptides (SB-37 and Shiva-1) in vitro. Human erythrocytes infected with *P. falciparum*, and Vero cells infected with *T. cruzi*, exposed to these peptides showed a significant decrease in the level of parasite infection. Furthermore, the peptides had a marked cytocidal effect on trypomastigote (Jaynes et at 1988) stages of *T. cruzi* in media, whereas host RBC were uninfected with this treatment.

In one embodiment, the cecropin is a cecropin A protein or nucleic acid. In another embodiment, the cecropin is a cecropin B protein or nucleic acid. In yet another embodiment, the cecropin is a cecropin C protein or nucleic acid. In yet a further embodiment, the cecropin is a cecropin D protein or nucleic acid.

The term "tail" as used herein refers to an amino acid sequence fused to the C-terminal end of the cecropin peptide.

The term "fused" as used herein refers to two nucleic acids fused together so that the resulting protein is expressed as a single protein. In particular, the 3' nucleic acid residue of the cecropin or variant thereof is bonded to the 5' nucleic acid residue of the tail.

Figure 11:
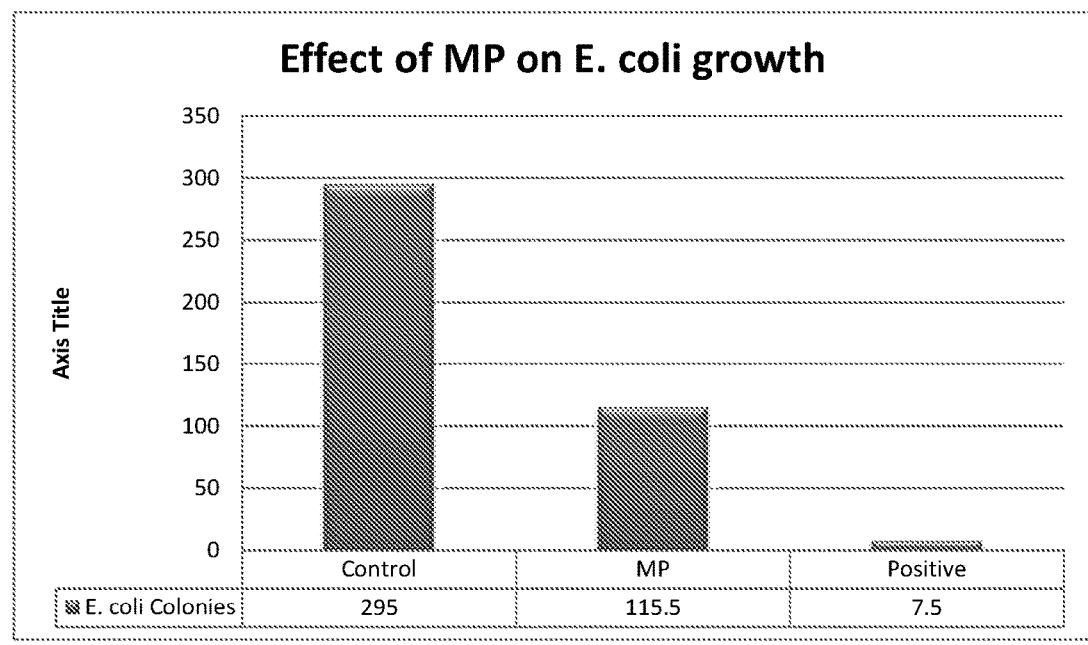
FIG. 11 shows reduction in *E. coli* numbers following treatment with modified cecropin. *E. coli* cells were grown overnight in LB broth at 37° C. Cells were serially diluted by up to $10^6$ cells/mL in water and split into 1 mL aliquots. The aliquots were split into three groups; Control, MP (cecropin) and Positive control. The control group was treated with 20 ug of total soluble protein extracted from the wild type CC11 yeast strain. The MP group was treated with 20 ug of total soluble protein extracted from a modified strain of yeast that expressed the modified anti-microbial peptide. The positive control group was treated with 50 ng of Ampicillin. Briefly, the treatments were added to the diluted cells and mixed thoroughly. The cells-protein mixtures were allowed to incubate for 20 min at 37° C. 100 uL from each tube was spread onto LB agar plate and incubated overnight at 37° C. The next day colonies on each plate were counted and averaged.
Figure 12A:
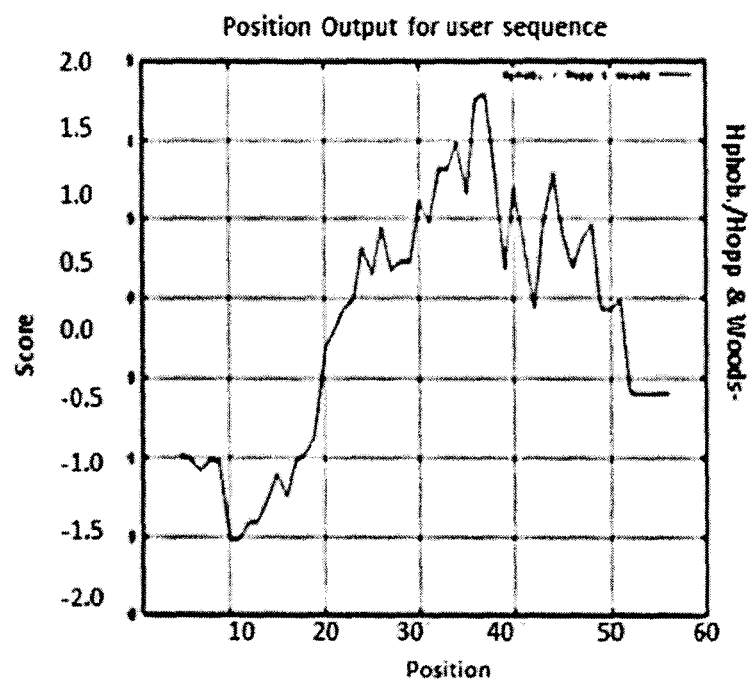
FIG. 12A shows the hydrophilicity plot of cecropin without a fusion tag. The amino acid sequence is shown above the graph (SEQ ID NO:13). The line above 1 is hydrophilic. The plot is deduced using Hoop T P and Woods K R (1981)
Figure 12B:
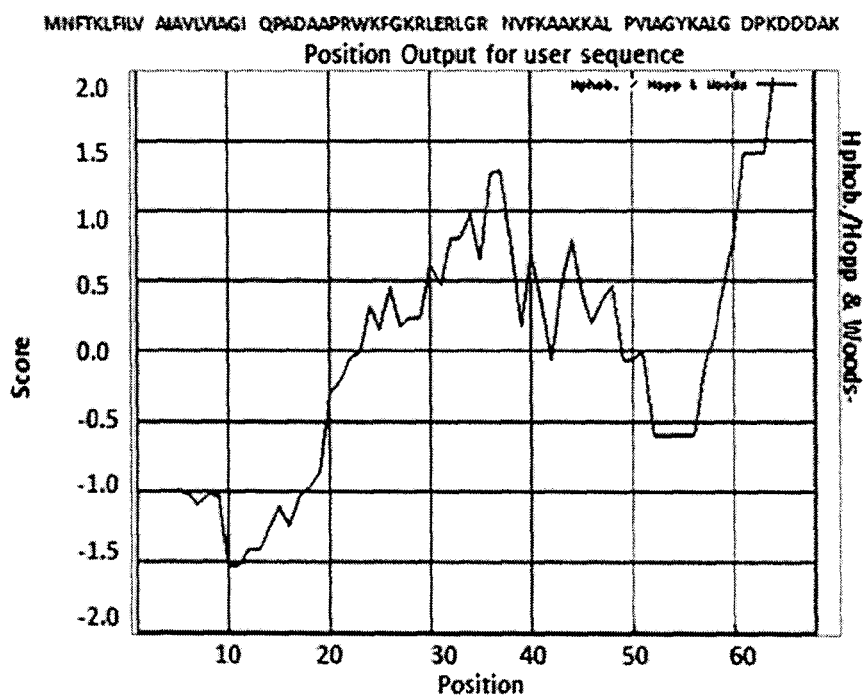
FIG. 12B shows the hydrophilicity plot of cecropin with an 8 amino acid fusion tag. The line above 1 indicates hydrophilic character. The sequence is shown above the graph (SEQ ID NO:2). The plot is deduced using Hoop T P and Woods K R (1981).
Figure 13A:
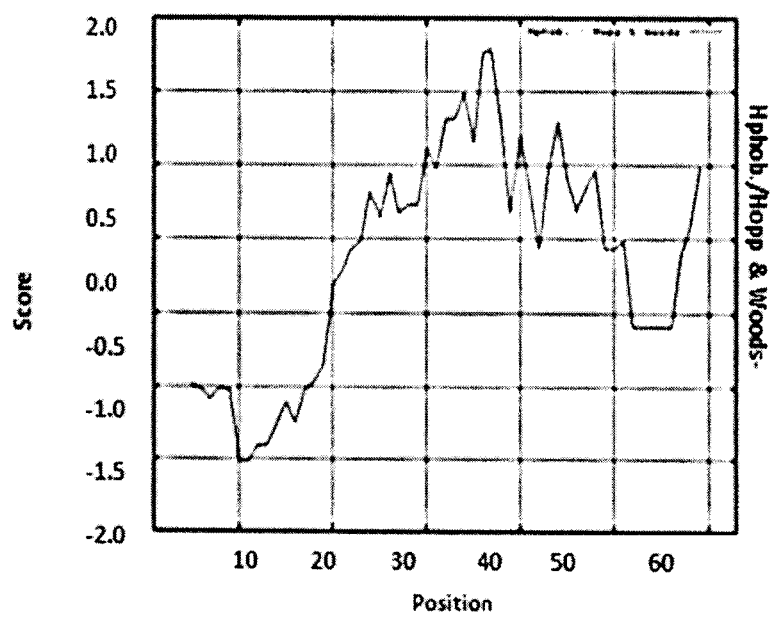
FIG. 13A shows the hydrophilicity plot of cecropin with a 3 amino acid fusion tag. The line above 1 indicates hydrophilic character. The sequence is shown above the graph (SEQ ID NO:10). The plot is deduced using Hoop T P and Woods K R (1981)
Figure 13B:
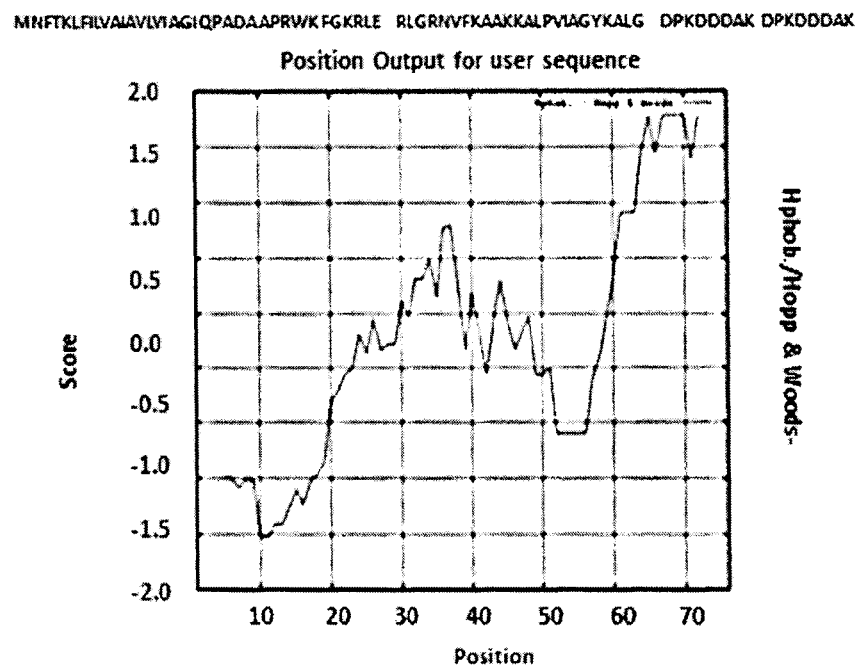
FIG. 13B shows the hydrophilicity plot of cecropin with a 16 amino acid fusion tag. The line above 1 indicates hydrophilic character. The sequence is shown above the graph (SEQ ID NO:6). The plot is deduced using Hoop T P and Woods K R (1981)
Figure 13C:
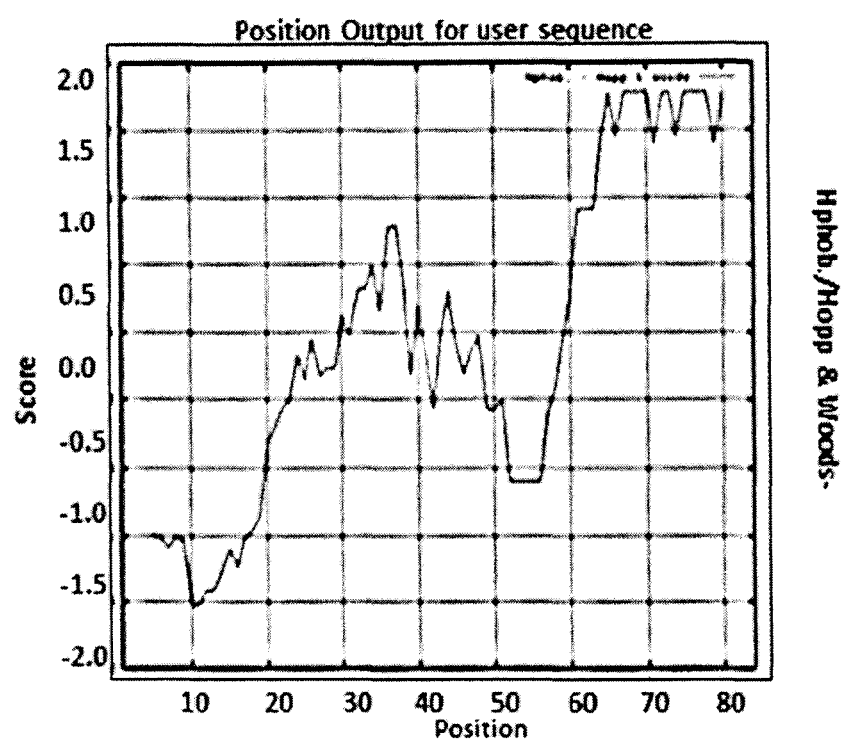
FIG. 13C shows the hydrophilicity plot of cecropin with 24 amino acid fusion tag. The line above 1 indicates hydrophilic character. The sequence is shown above the graph (SEQ ID NO:8). The plot is deduced using Hoop T P and Woods K R (1981)
Figure 13D:
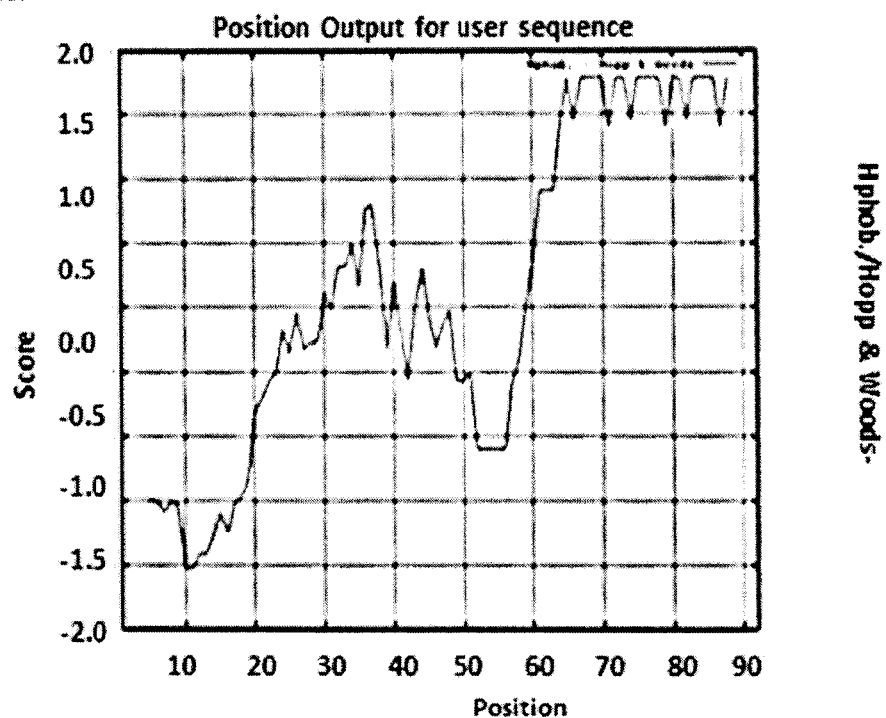
FIG. 13D shows the hydrophilicity plot of cecropin with a 32 amino acid fusion tag. The line above 1 indicates hydrophilic character. The sequence is shown above the graph (SEQ ID NO:12). The plot is deduced using Hoop T P and Woods K R (1981).

The term "hydrophilic" as used herein refers to the surface hydrophilicity (or affinity) of a protein and its stability against denaturation by solvents, such as water. Hydrophilicity of a peptide can be predicted using the Hoop-Woods scale (Hoop and Woods, 1981), which is designed to predict potentially antigenic regions of polypeptides. Values greater than zero are hydrophilic and are thus likely to be exposed on the surface of a folded protein. FIG. 11 shows the hydrophilicity of cecropin from Calvo et al. 2009 and the hydrophilicity of the same cecropin with an 8 amino acid hydrophilic tail. FIG. 12 shows the hydrophilicity of the same cecropin with 3, 16 and 24 amino acid hydrophilic tails as well as a 32 amino acid hydrophilic tail.

The phrase "lacking a C-terminal glycine residue" as used herein refers to the C-terminal residue of the resulting modified cecropin protein, which allows the protein to avoid amidation. The C-terminal residue of the modified cecropin is the last amino acid of the hydrophilic tail.

In one embodiment, the hydrophilic tail comprises 3 to 24 amino acids, optionally 8-16 amino acids. In one embodiment, the hydrophilic tail comprises a 3-24 amino acid sequence that provides a value of greater than 0 on a hydrophilicity plot. In an embodiment, the modified cecropin comprises the amino acid sequence as shown in SEQ ID NO:2 or a variant thereof. In another embodiment, the modified cecropin comprises the amino acid sequence as shown in SEQ ID NO:6 or a variant thereof. In yet another embodiment, the modified cecropin comprises the amino acid sequence as shown in SEQ ID NO:8 or a variant thereof. In a further embodiment, the modified cecropin comprises the amino acid sequence as shown in SEQ ID NO:10 or a variant thereof.

In another embodiment, the present disclosure provides a nucleic acid molecule encoding the modified cecropin disclosed herein. In one embodiment, the nucleic acid encodes a modified cecropin having the amino acid sequence as shown in SEQ ID NO:2, 6, 8 or 10 or a variant thereof or having the nucleic acid sequence as shown in SEQ ID NO:1, 5, 7 or 9 or a variant thereof.

The term "nucleic acid molecule" is intended to include unmodified DNA or RNA or modified DNA or RNA. For example, the nucleic acid molecules or polynucleotides of the disclosure can be composed of single- and double-stranded DNA, DNA that is a mixture of single- and double-stranded regions, single- and double-stranded RNA, and RNA that is a mixture of single- and double-stranded regions, hybrid molecules comprising DNA and RNA that may be single-stranded or, more typically double-stranded or a mixture of single- and double-stranded regions. In addition, the nucleic acid molecules can be composed of triple-stranded regions comprising RNA or DNA or both RNA and DNA. The nucleic acid molecules of the disclosure may also contain one or more modified bases or DNA or RNA backbones modified for stability or for other reasons. "Modified" bases include, for example, tritiated bases and unusual bases such as inosine. A variety of modifications can be made to DNA and RNA; thus "nucleic acid molecule" embraces chemically, enzymatically, or metabolically modified forms. The term "polynucleotide" shall have a corresponding meaning.

The term "variant" as used herein includes modifications, substitutions, additions, derivatives, analogs, fragments or chemical equivalents of the cecropin nucleic acid or amino acid sequences disclosed herein that perform substantially the same function in substantially the same way. For instance, the variants of the modified cecropin peptides would have the same function, for example, of stability and binding and lysing of endoparasites or bacteria. For example, the variant would not include a protein that inserts a glycine at the C-terminus of the modified protein. In one embodiment, the variant comprises a modification in the cecropin of the modified protein. In another embodiment, the variant comprises a modification in the hydrophilic tail of the modified protein.

Variants also include peptides with amino acid sequences that are substantially or essentially identical to the amino acid sequences of the modified cecropin protein or nucleic acid molecules with nucleic acid sequences that are substantially or essentially identical to the nucleic acid sequence encoding the modified cecropin proteins.

The term "substantially identical" or "essentially identical" as used herein means an amino acid sequence that, when optimally aligned, for example using the methods described herein, share at least 75%, 80%, 85%, 90%, 95%, 96%, 97%, 98%, 99%, or 100% sequence identity with a second amino acid sequence.

The term "sequence identity" as used herein refers to the percentage of sequence identity between two polypeptide and/or nucleotide sequences.

To determine the percent identity of two amino acid or nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleic acid residues at corresponding positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/total number of positions.times.100%). In one embodiment, the two sequences are the same length. The determination of percent identity between two sequences can also be accomplished using a mathematical algorithm. A preferred, non-limiting example of a mathematical algorithm utilized for the comparison of two sequences is the algorithm of Karlin and Altschul, 1990, Proc. Natl. Acad. Sci. U.S.A. 87:2264-2268, modified as in Karlin and Altschul, 1993, Proc. Natl. Acad. Sci. U.S.A. 90:5873-5877. Such an algorithm is incorporated into the NBLAST and XBLAST programs of Altschul et al., 1990, J. Mol. Biol. 215:403. BLAST nucleotide searches can be performed with the NBLAST nucleotide program parameters set, e.g., for score=100, wordlength=12 to obtain nucleotide sequences homologous to a nucleic acid molecule of the present disclosure. BLAST protein searches can be performed with the XBLAST program parameters set, e.g., to score-50, wordlength=3 to obtain amino acid sequences homologous to a protein molecule of the present disclosure. To obtain gapped alignments for comparison purposes, Gapped BLAST can be utilized as described in Altschul et al., 1997, Nucleic Acids Res. 25:3389-3402. Alternatively, PSI-BLAST can be used to perform an iterated search which detects distant relationships between molecules (Id.). When utilizing BLAST, Gapped BLAST, and PSI-Blast programs, the default parameters of the respective programs (e.g., of XBLAST and NBLAST) can be used (see, e.g., the NCBI website). Another non-limiting example of a mathematical algorithm utilized for the comparison of sequences is the algorithm of Myers and Miller, 1988, CABIOS 4:11-17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. The percent identity between two sequences can be determined using techniques similar to those described above, with or without allowing gaps. In calculating percent identity, typically only exact matches are counted.

The percentage of identity between two polypeptide sequences, the amino acid sequences of such two sequences are aligned, for example using the Clustal W algorithm (Thompson, J D, Higgins D G, Gibson T J, 1994, *Nucleic Acids Res.* 22(22): 4673-4680), together with BLOSUM 62 scoring matrix (Henikoff S, and Henikoff J. G., 1992, *Proc. Natl. Acad. Sci.* USA 89: 10915-10919) and a gap opening penalty of 10 and gap extension penalty of 0.1, so that the highest order match is obtained between two sequences wherein at least 50% of the total length of one of the sequences is involved in the alignment.

Other methods that may be used to align sequences are the alignment method of Needleman and Wunsch (Needleman and Wunsch. *J. Mol. Biol.,* 1970, 48:443), as revised by Smith and Waterman (Smith and Waterman. *Adv. Appl. Math.* 1981, 2:482) so that the highest order match is obtained between the two sequences and the number of identical amino acids is determined between the two sequences. Other methods to calculate the percentage identity between two amino acid sequences are generally art recognized and include, for example, those described by Carillo and Lipton (Carillo and Lipton *SIAM J. Applied Math.* 1988, 48:1073) and those described in Computational Molecular Biology (Computational Molecular Biology, Lesk, e.d. Oxford University Press, New York, 1988, *Biocomputing: Informatics and Genomics Projects*). Generally, computer programs will be employed for such calculations.

The term "analog" means an amino acid or nucleic acid sequence which has been modified as compared to the modified cecropin sequences disclosed herein wherein the modification does not alter the utility of the sequence (e.g. stability and binding to endoparasites and bacteria) as described herein. The modified sequence or analog may have improved properties over the modified cecropin sequences disclosed herein. One example of a nucleic acid modification to prepare an analog is to replace one of the naturally occurring bases (i.e. adenine, guanine, cytosine or thymidine) of the sequence with a modified base such as xanthine, hypoxanthine, 2-aminoadenine, 6-methyl, 2-propyl and other alkyl adenines, 5-halo uracil, 5-halo cytosine, 6-aza uracil, 6-aza cytosine and 6-aza thymine, pseudo uracil, 4-thiouracil, 8-halo adenine, 8-aminoadenine, 8-thiol adenine, 8-thiolalkyl adenines, 8-hydroxyl adenine and other 8-substituted adenines, 8-halo guanines, 8 amino guanine, 8-thiol guanine, 8-thiolalkyl guanines, 8-hydroxyl guanine and other 8-substituted guanines, other aza and deaza uracils, thymidines, cytosines, adenines, or guanines, 5-trifluoromethyl uracil and 5-trifluoro cytosine.

Another example of a modification is to include modified phosphorous or oxygen heteroatoms in the phosphate backbone, short chain alkyl or cycloalkyl intersugar linkages or short chain heteroatomic or heterocyclic intersugar linkages in the nucleic acid molecules. For example, the nucleic acid sequences may contain phosphorothioates, phosphotriesters, methyl phosphonates, and phosphorodithioates.

A further example of an analog of a nucleic acid molecule of the disclosure is a peptide nucleic acid (PNA) wherein the deoxyribose (or ribose) phosphate backbone in the DNA (or RNA), is replaced with a polyamide backbone which is similar to that found in peptides (P. E. Nielsen, et al Science 1991, 254, 1497). PNA analogs have been shown to be resistant to degradation by enzymes and to have extended lives in vivo and in vitro. PNAs also bind stronger to a complementary DNA sequence due to the lack of charge repulsion between the PNA strand and the DNA strand. Other nucleic acid analogs may contain nucleotides containing polymer backbones, cyclic backbones, or acyclic backbones. For example, the nucleotides may have morpholino backbone structures (U.S. Pat. No. 5,034,506). The analogs may also contain groups such as reporter groups, a group for improving the pharmacokinetic or pharmacodynamic properties of nucleic acid sequence.

The modified cecropin proteins disclosed herein may be modified to contain amino acid substitutions, insertions and/or deletions that do not alter the stability and/or binding and/or activating properties of the protein. Conserved amino acid substitutions involve replacing one or more amino acids of the protein with amino acids of similar charge, size, and/or hydrophobicity characteristics. When only conserved substitutions are made the resulting analog should be functionally equivalent to the modified cecropin disclosed herein. Non-conserved substitutions involve replacing one or more amino acids of the conjugate protein with one or more amino acids which possess dissimilar charge, size, and/or hydrophobicity characteristics.

The disclosure further encompasses nucleic acid molecules that differ from any of the nucleic acid molecules disclosed herein in codon sequences due to the degeneracy of the genetic code.

Also included is a vector comprising a nucleic acid molecule disclosed herein. Such a vector also comprises the necessary regulatory sequences for the transcription and translation of the inserted sequence. Suitable regulatory sequences may be derived from a variety of sources, including bacterial, fungal, viral, mammalian, or insect genes (for example, see the regulatory sequences described in Goeddel, Gene Expression Technology: Methods in Enzymology 185, Academic Press, San Diego, Calif. (1990)). Selection of appropriate regulatory sequences is dependent on the host cell chosen as discussed below, and may be readily accomplished by one of ordinary skill in the art. Examples of such regulatory sequences include: a transcriptional promoter and enhancer or RNA polymerase binding sequence, a ribosomal binding sequence, including a translation initiation signal. Additionally, depending on the host cell chosen and the vector employed, other sequences, such as an origin of replication, additional DNA restriction sites, enhancers, and sequences conferring inducibility of transcription may be incorporated into the expression vector. It will also be appreciated that the necessary regulatory sequences may be supplied by cecropin sequences and/or its flanking regions.

Further provided is a host cell comprising a vector disclosed herein.

Recombinant expression vectors can be introduced into host cells to produce a transformed host cell. The term "transformed host cell" is intended to include cells that are capable of being transformed or transfected with a recombinant expression vector of the disclosure. The terms "transduced", "transformed with", "transfected with", "transformation" and "transfection" are intended to encompass introduction of nucleic acid (e.g. a vector or naked RNA or DNA) into a cell by one of many possible techniques known in the art. Prokaryotic cells can be transformed with nucleic acid by, for example, electroporation or calcium-chloride mediated transformation. For example, nucleic acid can be introduced into mammalian cells via conventional techniques such as calcium phosphate or calcium chloride co-precipitation, DEAE-dextran mediated transfection, lipofectin, electroporation, microinjection, RNA transfer, DNA transfer, artificial chromosomes, viral vectors and any emerging gene transfer technologies. Suitable methods for transforming and transfecting host cells can be found in Sambrook et al. (Molecular Cloning: A Laboratory Manual, 2nd Edition, Cold Spring Harbor Laboratory press (1989)), and other laboratory textbooks.

Suitable expression vectors for directing expression in mammalian cells generally include a promoter (e.g., derived from viral material such as polyoma, Adenovirus 2, cytomegalovirus and Simian Virus 40), as well as other transcriptional and translational control sequences. Examples of mammalian expression vectors include pCDM8 (Seed, B., Nature 329:840 (1987)), pMT2PC (Kaufman et al., EMBO J. 6:187-195 (1987)) and pCMV (Clontech, Calif., U.S.A.).

Suitable host cells include a wide variety of prokaryotic and eukaryotic host cells. For example, the proteins of the disclosure may be expressed in bacterial cells such as E. coli, insect cells (using baculovirus), yeast cells, algal cells or mammalian cells. Other suitable host cells can be found in Goeddel (Goeddel, Gene Expression Technology: Methods in Enzymology 185, Academic Press, San Diego, Calif. 1990). In one embodiment, the host cell is a yeast cell. In another embodiment, the host cell is an algal cell.

The proteins disclosed herein may also be prepared by chemical synthesis using techniques well known in the chemistry of proteins such as solid phase synthesis (Merrifield, J. Am. Chem. Assoc. 85:2149-2154 (1964); Frische et al., J. Pept. Sci. 2(4): 212-22 (1996)) or synthesis in homogenous solution (Houbenweyl, Methods of Organic Chemistry, ed. E. Wansch, Vol. 15 I and II, Thieme, Stuttgart (1987)).

The term "isolated amino acid sequence" refers to an amino acid substantially free of cellular material or culture medium when produced by recombinant techniques.

Pharmaceutical Compositions

In yet another embodiment, the present disclosure provides a pharmaceutical composition comprising a modified cecropin disclosed herein, a nucleic acid disclosed herein, a vector disclosed herein or a host cell disclosed herein, and a pharmaceutically acceptable carrier.

The pharmaceutical compositions can be prepared by per se known methods for the preparation of pharmaceutically acceptable compositions which can be administered to patients, and such that an effective quantity of the active substance is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 2003—20$^{th}$ Edition) and in The United States Pharmacopeia: The National Formulary (USP 24 NF19) published in 1999).

On this basis, the pharmaceutical compositions include, albeit not exclusively, the active compound or substance in association with one or more pharmaceutically acceptable vehicles or diluents, and contained in buffered solutions with a suitable pH and iso-osmotic with the physiological fluids. The pharmaceutical compositions may additionally contain other agents such as other anti-malarial agents. For example, for a malarial infection, typical agents include, but are not limited to, the drugs Amodiaquine, Artemisinin and derivatives, Atovaquone, Clindamycin, Chloroquine and hydroxychloroquine, Doxycycline, Halofantrine, Mefloquine, Primaquine, Proguanil, Pyrimethamine, Sulfonamides.

Methods and Uses

In a further embodiment, the present disclosure provides a method of inhibiting an endoparasite or bacterium comprising administering a modified cecropin disclosed herein, a nucleic acid disclosed herein, a vector disclosed herein or a host cell disclosed herein to an animal in need thereof. Also provided herein is a use of a modified cecropin disclosed herein, a nucleic acid disclosed herein, a vector disclosed herein or a host cell disclosed herein for inhibiting an endoparasite or bacterium in an animal in need thereof. Further provided herein is a use of a modified cecropin disclosed herein, a nucleic acid disclosed herein, a vector disclosed herein or a host cell disclosed herein in the preparation of a medicament for inhibiting an endoparasite or bacterium in an animal in need thereof. Even further provided herein is a modified cecropin disclosed herein, a nucleic acid disclosed herein, a vector disclosed herein or a host cell disclosed herein for use in inhibiting an endoparasite or bacterium in an animal in need thereof.

In one embodiment, there is provided a method of inhibiting an endoparasite or bacterium comprising administering a cecropin or variant thereof fused to a hydrophilic tail lacking a C-terminal glycine. Also provided herein is use of a cecropin or variant thereof fused to a hydrophilic tail lacking a C-terminal glycine for inhibiting an endoparasite or bacterium in an animal in need thereof. Further provided is use of a cecropin or variant thereof fused to a hydrophilic tail lacking a C-terminal glycine in the preparation of a medicament for inhibiting an endoparasite or bacterium in an animal in need thereof. Even further provided is a cecropin or variant thereof fused to a hydrophilic tail lacking a C-terminal glycine for use in inhibiting an endoparasite or bacterium in an animal in need thereof.

The term "endoparasite" as used herein refers to an organism that lives in/on another organism (animal) and it obtains nourishment from the host without benefiting or killing the host, and includes, without limitation, protozoan parasites, such as Coccidia (e.g. *Cryptosporidium*), *Leishmania, Plasmodia, Toxoplasma, Trichomonas*, and *Trypanosoma* and Helminth parasites such as Toxocara and *Fasciola*; animal parasites such as Ascarids, Toxocara, Toxascaris, *Ancylostoma* (Hookworms), *Trichuris* (Whipworms), *Dirofilaria* (Heartworms) and Angiostrongylidae (Lungworms).

The term "bacterium" as used herein refers to a prokaryotic microorganism that causes a bacterial infection, including without limitation, *E. Coli, Pseudomonas, Enterobactor, Klebsiella, Pneumoniae, Aerococcus, Bacillus cereus, Lactobacillus, Monococcus, Staphylococcus*, and *Streptococcus* infections.

The phrase "inhibiting an endoparasite or bacterium" as used herein refers to inhibiting the growth or activity of endoparasites or bacteria, for example, by binding and/or lysing the membrane of the endoparasite or bacterium.

In a further embodiment, the present disclosure provides a method of treating or preventing an endoparasite or bacterial infection comprising administering a modified cecropin disclosed herein, a nucleic acid disclosed herein, a vector disclosed herein or a host cell disclosed herein to an animal in need thereof. Also provided herein is a use of a modified cecropin disclosed herein, a nucleic acid disclosed herein, a vector disclosed herein or a host cell disclosed herein for treating or preventing an endoparasite or bacterial infection in an animal in need thereof. Further provided herein is a use of a modified cecropin disclosed herein, a nucleic acid disclosed herein, a vector disclosed herein or a host cell disclosed herein in the preparation of a medicament for treating or preventing an endoparasite or bacterial infection in an animal in need thereof. Even further provided herein is a modified cecropin disclosed herein, a nucleic acid disclosed herein, a vector disclosed herein or a host cell disclosed herein for use in treating or preventing an endoparasite or bacterial infection in an animal in need thereof.

In one embodiment, the endoparasite is malaria. The term "malaria" as used herein refers to an infection caused by a parasite belonging to the genus *Plasmodium*. Malarial species that typically cause human infection include, without limitation, *P. falciparum, P. ovale, P. vivax* and *P. malariae*.

In another embodiment, the bacterium is *E. coli* or *Pseudomonas*.

The term "administering a cecropin or variant thereof fused to a hydrophilic tail lacking a C-terminal glycine" includes both administration of the modified cecropin protein as well as administration of a nucleic acid encoding the modified cecropin protein to an animal or to a cell in vivo or in vitro.

The cecropins disclosed herein may be administered in vivo or ex vivo to a cell which is then administered. For example, cells may be transformed or transduced with the nucleic acid encoding the protein disclosed herein and then the cells are administered in vivo.

The term "treating" or "treatment" as used herein means administering to a subject a therapeutically effective amount of the compositions, nucleic acids or proteins of the present disclosure and may consist of a single administration, or alternatively comprise a series of applications.

As used herein, and as well understood in the art, "treatment" or "treating" is also an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment. Further any of the treatment methods or uses described herein can be formulated alone or for contemporaneous administration with other agents or therapies. "Treatment" or "treating" can also include preventing the onset of disease.

The term a "therapeutically effective amount", "effective amount" or a "sufficient amount" of a compound or composition of the present disclosure is a quantity sufficient to, when administered to the subject, including a mammal, for example a human, effect beneficial or desired results, including clinical results, and, as such, an "effective amount" or synonym thereto depends upon the context in which it is being applied. For example, in the context of treating malaria, for example, it is an amount of the compound or composition sufficient to achieve such a treatment as compared to the response obtained without administration of the compound or composition. In the context of malaria, therapeutically effective amounts of the compounds or compositions disclosed herein are used to treat, modulate, attenuate, reverse, or affect malarial infections in a mammal. An "effective amount" is intended to mean that amount of a compound or composition that is sufficient to treat, prevent or inhibit endoparasitic, such as malarial, and bacterial infections. In some suitable embodiments, the amount of a given compound or composition will vary depending upon various factors, such as the given drug or compound, the pharmaceutical formulation, the route of administration, the type of disease or disorder, the identity of the subject or host being treated, and the like, but can nevertheless be routinely determined by one skilled in the art. Also, as used herein, a "therapeutically effective amount" of a compound or composition of the present disclosure is an amount which prevents, inhibits, suppresses or reduces infections in a subject as compared to a control. As defined herein, a therapeutically effective amount of a compound or composition of the present disclosure may be readily determined by one of ordinary skill by routine methods known in the art.

The term "subject" or "animal" as used herein includes all members of the animal kingdom including mammals, suitably humans including patients.

In accordance with the methods disclosed herein, the modified cecropin proteins, nucleic acids, vectors or cells, may be administered to a patient in a variety of forms depending on the selected route of administration, as will be understood by those skilled in the art. The compounds or compositions may be administered, for example, by oral, parenteral, buccal, sublingual, nasal, rectal, patch, pump or transdermal administration and the pharmaceutical compositions formulated accordingly. Parenteral administration includes intravenous, intraperitoneal, subcutaneous, intramuscular, transepithelial, nasal, intrapulmonary, intrathecal, rectal and topical modes of administration. Parenteral administration may be by continuous infusion over a selected period of time.

The compounds or compositions may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the compound or composition may be incorporated with excipient and used in the form of ingestible tablets, buccal tablets, troches, capsules, elixirs, suspensions, syrups, wafers, and the like.

The compounds or compositions disclosed herein may also be administered parenterally. Solutions can be prepared in water suitably mixed with a surfactant such as hydroxypropylcellulose. Dispersions can also be prepared in glycerol, liquid polyethylene glycols, DMSO and mixtures thereof with or without alcohol, and in oils. Under ordinary conditions of storage and use, these preparations contain a preservative to prevent the growth of microorganisms. A person skilled in the art would know how to prepare suitable formulations. Conventional procedures and ingredients for the selection and preparation of suitable formulations are described, for example, in Remington's Pharmaceutical Sciences (2000-20th edition) and in The United States Pharmacopeia: The National Formulary (USP 24 NF19) published in 1999.

The pharmaceutical forms suitable for injectable use include sterile aqueous solutions or dispersion and sterile powders for the extemporaneous preparation of sterile injectable solutions or dispersions. In all cases, the form must be sterile and must be fluid to the extent that easy syringability exists.

Compositions for nasal administration may conveniently be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomising device. Alternatively, the sealed container may be a unitary dispensing device such as a single dose nasal inhaler or an aerosol dispenser fitted with a metering valve which is intended for disposal after use. Where the dosage form comprises an aerosol dispenser, it will contain a propellant which can be a compressed gas such as compressed air or an organic propellant such as fluorochlorohydrocarbon. The aerosol dosage forms can also take the form of a pump-atomizer.

Compositions suitable for buccal or sublingual administration include tablets, lozenges, and pastilles, wherein the active ingredient is formulated with a carrier such as sugar, acacia, tragacanth, or gelatin and glycerine. Compositions for rectal administration are conveniently in the form of suppositories containing a conventional suppository base such as cocoa butter.

The proteins, nucleic acids, vectors and cells disclosed herein may be used alone or in combination with other known agents useful for treating or preventing an endoparasite or bacterial infection. For example, for a malarial infection, typical treatments include, but are not limited to, the drugs Amodiaquine, Artemisinin and derivatives, Atovaquone, Clindamycin, Chloroquine and hydroxychloroquine, Doxycycline, Halofantrine, Mefloquine, Primaquine, Proguanil, Pyrimethamine, Sulfonamides. Preventative treatments such as vaccination, treated or untreated nets, spraying are also included. For a bacterial infection, typical treatments include antibiotics, such as tetracycline, penicillin, chloramphenicol, and ampicillin.

When used in combination with other agents useful in treating or preventing endoparasitic or bacterial infections, the compounds are suitably administered contemporaneously with those agents. As used herein, "contemporaneous administration" of two substances to an individual means providing each of the two substances so that they are both biologically active in the individual at the same time. The exact details of the administration will depend on the pharmacokinetics of the two substances in the presence of each other, and can include administering the two substances within a few hours of each other, or even administering one substance within 24 hours of administration of the other, if the pharmacokinetics are suitable. Design of suitable dosing regimens is routine for one skilled in the art. In particular embodiments, two substances will be administered substantially simultaneously, i.e., within minutes of each other, or in a single composition that contains both substances.

The proteins, nucleic acids, vectors and cells disclosed herein may be administered to an animal alone or also in combination with pharmaceutically acceptable carriers, as noted above, the proportion of which is determined by the solubility and chemical nature of the compound, chosen route of administration and standard pharmaceutical practice.

The dosage of the proteins, nucleic acids, vectors and cells disclosed herein can vary depending on many factors such as the pharmacodynamic properties of each, the mode of administration, the age, health and weight of the recipient, the nature and extent of the symptoms, the frequency of the treatment and the type of concurrent treatment, if any, and the clearance rate of each in the animal to be treated. One of skill in the art can determine the appropriate dosage based on the above factors. Proteins, nucleic acids, vectors and cells disclosed herein may be administered initially in a suitable dosage that may be adjusted as required, depending on the clinical response.

The above disclosure generally describes the present application. A more complete understanding can be obtained by reference to the following specific examples. These examples are described solely for the purpose of illustration and are not intended to limit the scope of the disclosure. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present disclosure:

EXAMPLES

Materials and Methods

Gene Syntheses

The cecropin gene sequence from Calvo et al. (2009) was codon optimised for expression in yeast cells and a hydrophilic tail of eight amino acids in length was added to it. The nucleic acid and amino sequences of the resulting cecropin are shown in Table 1 and 2, respectively. This gene was inserted into a plasmid.

Plasmid Construction

The cecropin gene was cut from the carrier plasmid with appropriate restriction enzymes purified and ligated into the plasmid, a Leu2 yeast vector, at the Bmtl-Mlul site (See FIG. 1). The clones were checked by further digestion with restriction enzymes specific for the Bmtl and Mlul loci.

Cloning and Transformation Strategy

Transformation into yeast was carried out using 'Gietz & Woods' Yeast Transformation Protocol using LiAc. [Geitz R D & R A Woods, 2002]. Transformed clones were tested for the presence of the gene by PCR using the primers: CECR- F: GTATCCAACCTGCCGATGCT (SEQ ID NO:3) and CECR-R: GCTAGCTCATTTGTCGTCATCG (SEQ ID NO:4).

Expression in Yeast

To confirm expression, yeast was lysed using the standard 'glass beads' method and assayed to determine their concentration. An aliquot of transformed yeast extract was electrophoresed together with a control, non-transformed yeast, in a polyacrylamide gel and transferred onto a PDF membrane. The membrane was then hybridised with cecropin specific antibody. A chemiluminescent dye was used to read the positive samples using BioRad gel doc system.

Assay of Bacterial Activity

Once the expression level of the positive clones was established, the yeast extract was assayed for antimicrobial activity. An aliquot of an overnight culture of E. coli was cultured for 4 hours at 37° C. The culture was checked for growth using a spectrophotometer and $10^7$ bacteria were used to dilute, 10 fold, with PBS. A constant concentration of yeast extract was added to each tube, incubated for 2 hours and plated onto agar plates. Ampicillin was used as a positive control. Plates were incubated at 37° C. overnight and a plate count was made to see the effect of the expressed modified cecropin.

In Vitro Efficacy

The parasite, P. falciparum, was exposed to cecropin in vitro using an assay for lactate dehydrogenase (LDH) that was made specific for the Plasmodium parasite's LDH enzyme by the substitution of APAD for NAD. The presence of LDH activity distinguishes between live and dead Plasmodia. A standard number of malarial parasites was added to each well of a 96 well plate. The cecropin-yeast extract was serially diluted across the plate. Parasite viability was measured by activity of the enzyme LDH. From these data, a calculation was made of the concentration of protein (µg) in the samples that killed 50% of the parasites ($IC_{50}$).

Toxicity Test

A hundred times the $IC_{50}$ concentration of yeast extract (deduced from the in-vitro test) was used to test the toxicity of the samples in mice (strain CD-1, 18-23 gms individual weight). The yeast extracts were administered either by intraperitoneal injection (no anaesthesia) or perorally. 500 µl of control or cecropin-yeast extract was delivered by oral gavage directly into the stomach or by IP injection. Five mice in each group were used for the test. The trial was conducted according to the United States Pharmacopeia regulations. Daily observation of clinical signs of toxicity were monitored (anorexia, vomiting, diarrhoea, recumbency, appetite, water intake, behavioural signs of distress (hovering in corner, pacing, panting and failing to groom). Animals were checked twice daily.

Permeability Test

A hundred times the $IC_{50}$ concentration of yeast extract (deduced from the in-vitro test) was used to test the permeability of cecropin through the gut wall of the mice (Strain CD-1, 18-23 gms individual weight). The yeast extracts were administered either by intraperitoneal injection or perorally. 500 µl of control or cecropin-yeast extract was delivered by IP injection or by oral gavage directly into the stomach. Five mice in each group were used for the test. The trial was conducted according to the United States Pharmacopeia regulations. Forty-eight hours later 100-200 µl each of blood serum and blood plasma were collected into sterile tubes by cardiac puncture and the samples frozen at minus 80° C. until use.

In-Vivo Efficacy Assay

Mice were infected with $10^6$ parasitized red blood cells and then monitored for parasitemia for several days. Typically parasites can first be detected at Day 4-5 post infection. The mice were infused with control or cecropin-yeast extract at either high or low doses on Day 4 and blood samples were taken daily up to Day 14. These were examined to determine parasitemia. The number of parasites chosen to infect the animals was designed to produce an initial infection that neither overwhelms the animal, nor permits the animals to clear the infections easily. It is also the method used to examine how differences in immunity in animals correlate with outcome; treatments that themselves weaken the animals will promote the infection, treatments that target the parasite exclusively will provide a marked benefit. The general health parameters (body weight, anorexia, movement etc.) of the mice were noted during the experiment.

Results

In Vitro Evaluation of Efficacy

A 96-well plate was prepared by adding growth media and a uniform number of malarial parasites to each well. This was incubated for 48 hours at 37° C. following which the malarial cells were remixed and a crude yeast lysate sample containing cecropin was then added and diluted across the plate to give a concentration gradient. Plasmodium contains a Lactate Dehydrogenase that has an unusual NAD analogue preference and therefore can be used as an indicator of parasite specific viability. Viable parasites cause the assay to turn blue, which is then read using a plate reader. From these colour density readings an $IC_{50}$ value is calculated; the lower the concentration at which an $IC_{50}$ is estimated, the more lethal is the material under test.

Figure 3:
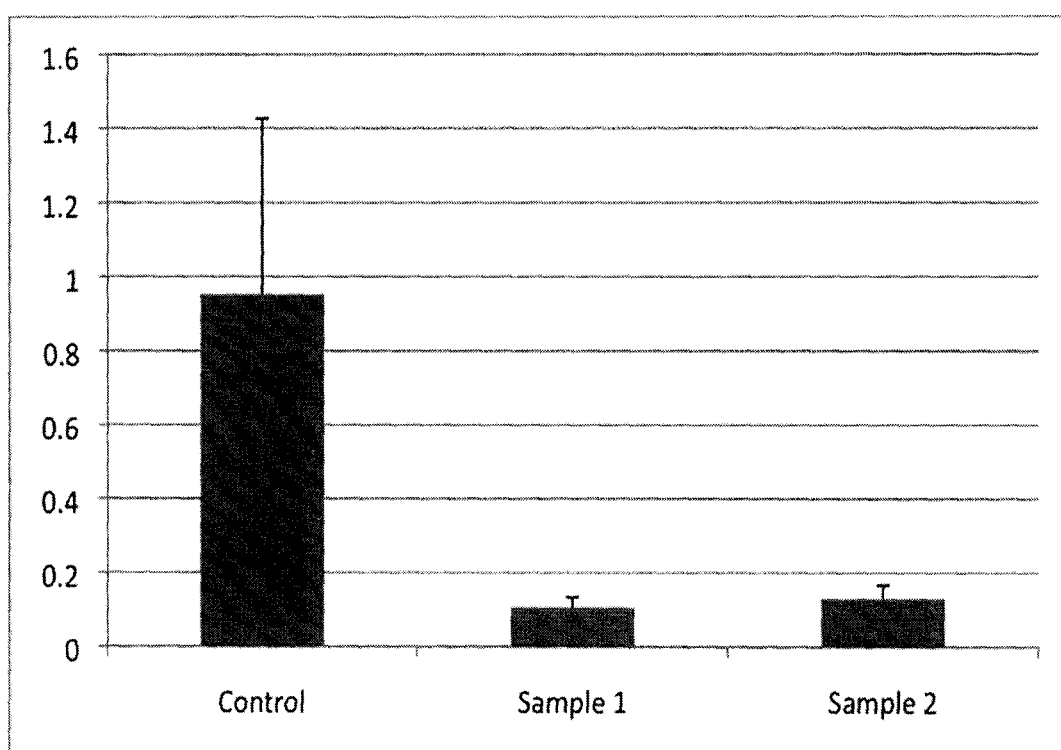
FIG. 3 shows the IC50 values for lethality of *Plasmodium falciparum* by yeast expressing modified cecropin.

It was determined in a series of tests that the $IC_{50}$ value for "Control" yeast, i.e. not expressing cecropin, was 0.95 µg/ml. Two independently prepared growths of yeast expressing cecropin gave values of 0.12 and 0.13 µg/ml. These differences were significant and are shown in FIG. 3.

In Vivo Trial 1:

To Evaluate the Effect of Administering Yeast Expressing a Modified Form of the Naturally Occurring Protein Cecropin Administered by Injection at Three Time Points.

Mice were infected with $10^6$ parasitised red blood cells and the resulting parasitemia was monitored for 8 days. The day of infection was designated Day 0 and parasites were first observed on Day 4. On Days 4, 5 and 6 the mice were infused with either Control yeast (not expressing cecropin) or with cecropin expressing yeast at either 0.36 mg/mouse or 0.072 mg per mouse (high and low doses, respectively). On each of these days blood samples were taken and examined to determine parasitemia.

Figure 4:
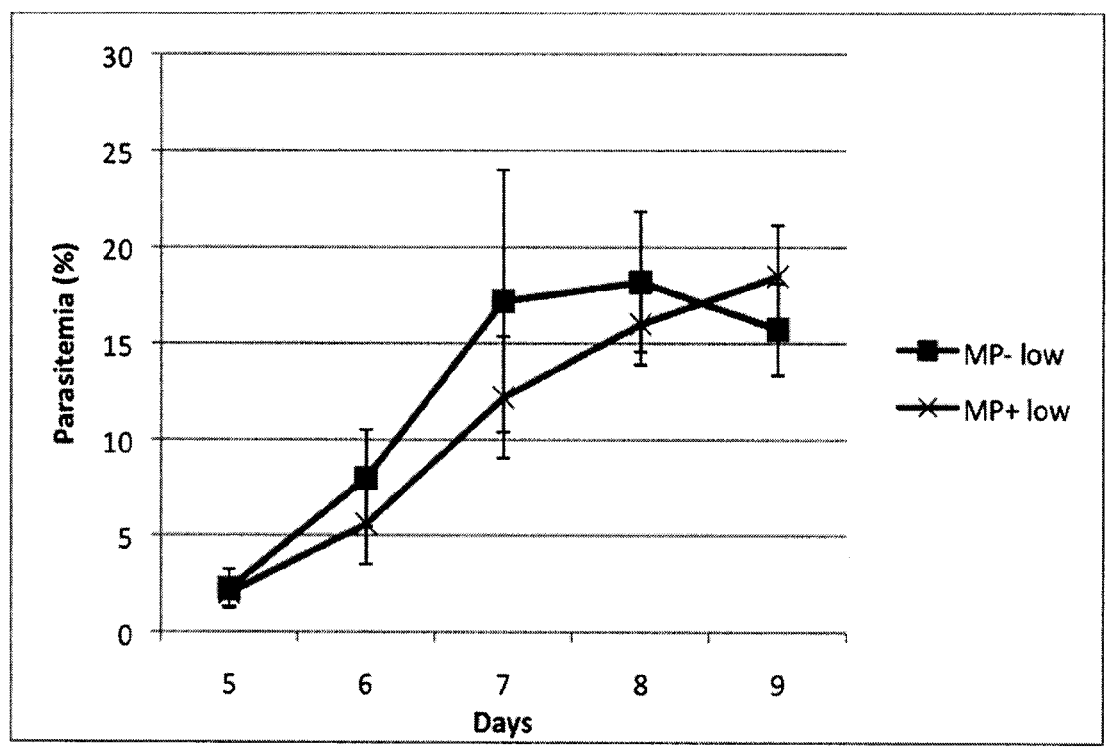
FIG. 4 shows percentage of parasitemia after administration of a low dose of yeast expressing modified cecropin.

In the data shown in FIG. 4 for the low dose administration there is a significant suppression of parasite numbers on Day 6 and a supporting trend, approaching significance between day 5 to day 7. The Control numbers are consistent with expectation for untreated, control mice with a rapid increase in parasitemia over several days and a plateau which is reached at around day 7-8.

Figure 5:
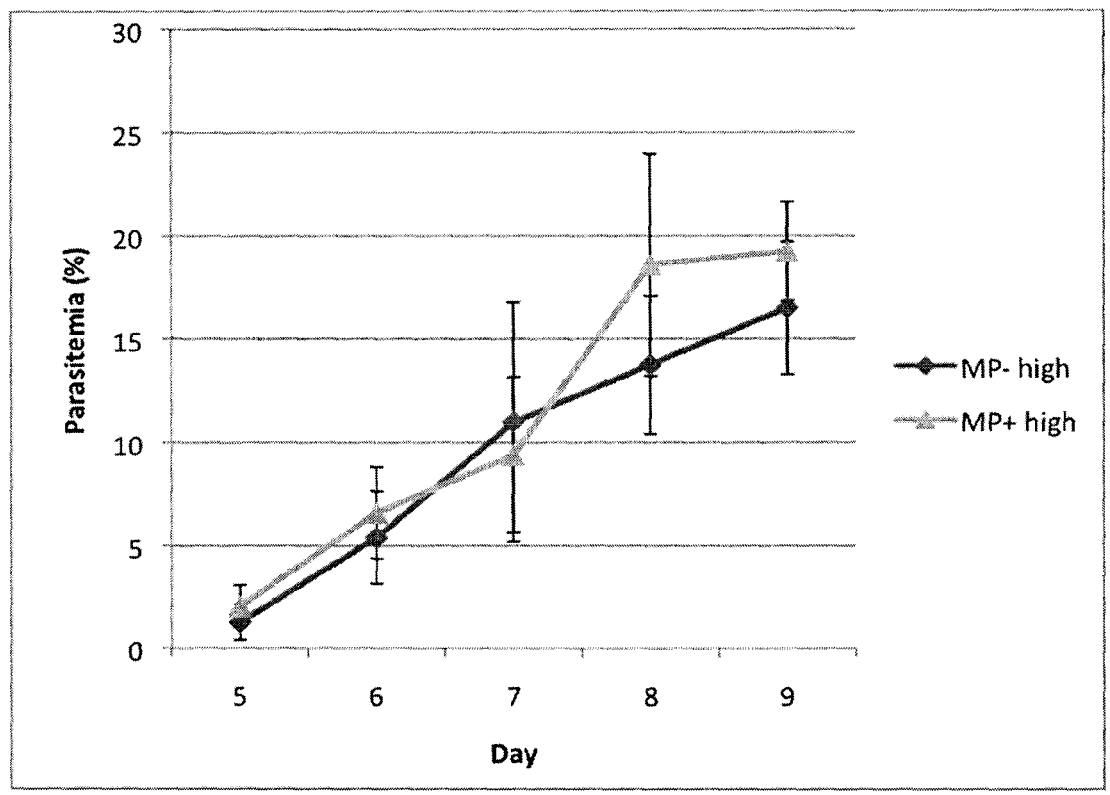
FIG. 5 shows percentage of parasitemia after administration of a high dose of yeast expressing modified cecropin.

In the data shown in FIG. 5 for the high dose administration, there were no significant differences between the groups. However the progression of the parasitemia in the Control group is not consistent with a typical, untreated mouse group which suggests that high dose, control yeast may have been influencing the outcome of the infection.

Throughout the trial, mice treated with the modified cecropin expressing yeast appeared to be stronger.

The trial was terminated at day 8.

Figure 6:
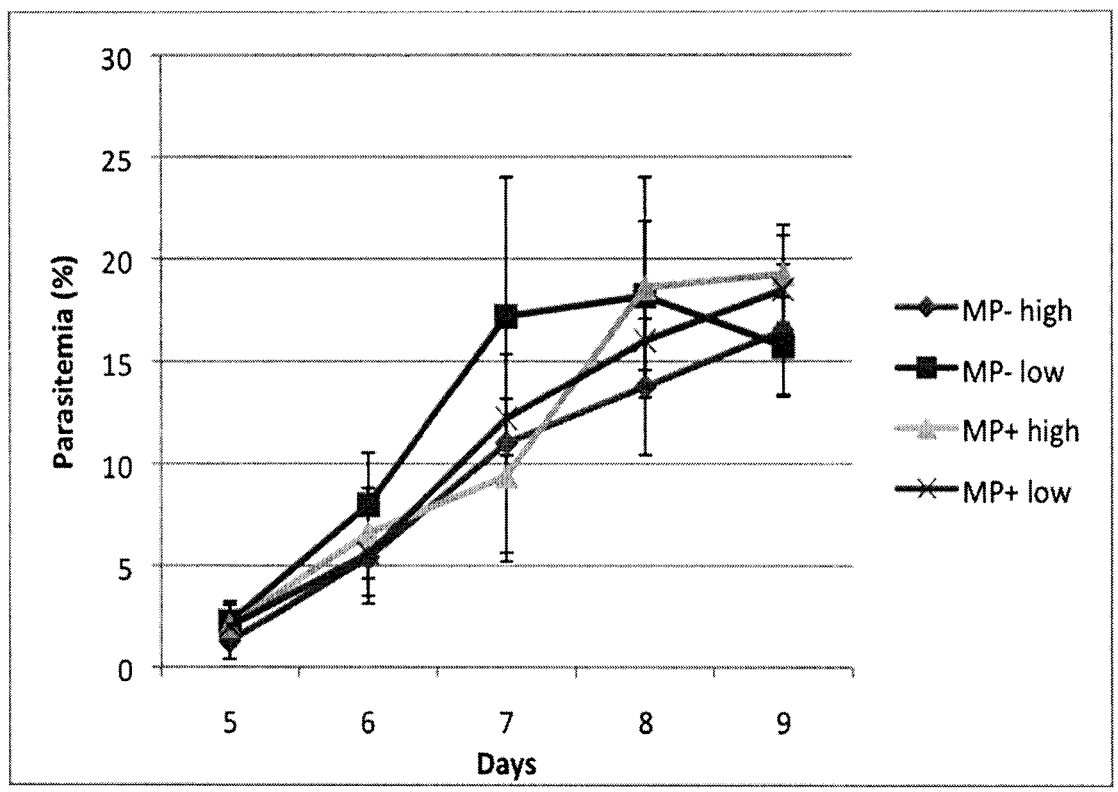
FIG. 6 shows percentage of parasitemia with high and low doses of yeast expressing modified cecropin administered to mice on days 5-7 post-infection.

In summary, the animals injected with the control, low dose yeast, showed a typical infection whereas those administered low-dose cecropin suppressed, but did not eliminate, the parasites. The outcome of the higher dose experiment was not as clear since the control mice did not undergo a typical infection (See FIG. 6 for combined low and high dose).

In Vivo Trial 2:

To Evaluate the Effect of Administering Yeast Expressing a Modified Form of the Naturally Occurring Protein Cecropin Administered by Infection at Three Time Points.

In this trial, mice were injected with the cecropin yeast at three different time points starting on the first day at which signs of infection were detected.

Figure 7:
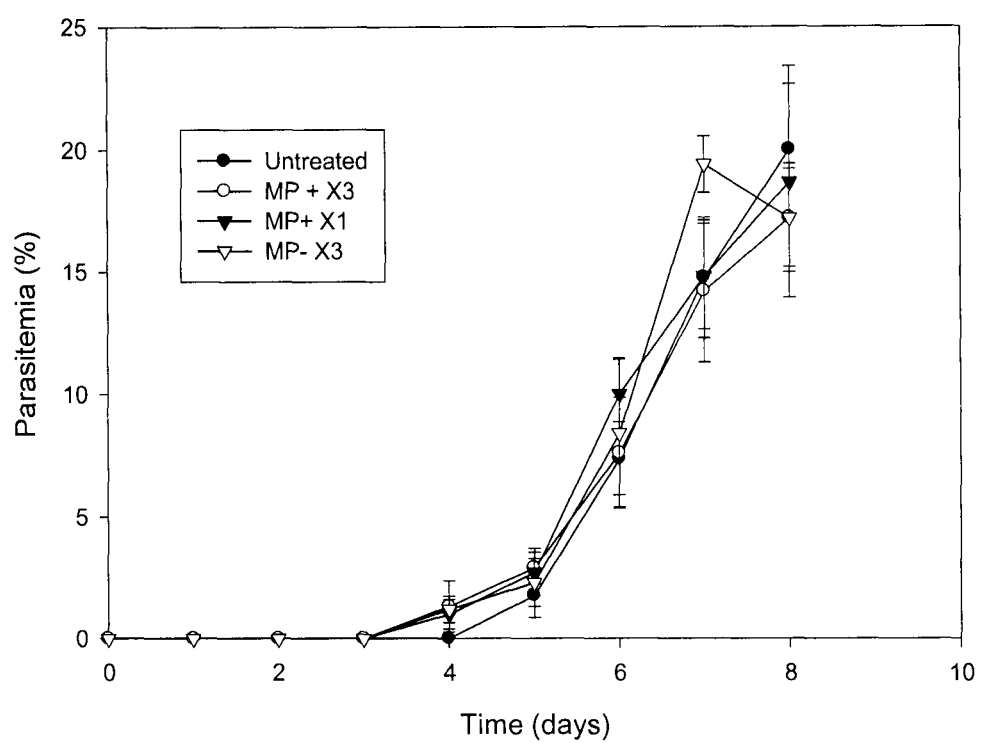
FIG. 7 shows the percentage of parasitemia with high dose of yeast extract expressing modified cecropin administered once and 3 times in comparison with high dose of yeast extract without cecropin administered 3 times and also an untreated group.

To initiate infection, mice were infected with $4 \times 10^5$ parasites on Day 0. Parasites were first observed in the blood of the mice on Day 5. On Day 5, Group A (untreated control) was administered RPMI 1640 (cell growth medium), Group B was administered a "high dose" (determined from Trial 1) of 0.35 mg yeast lysate (105 ng actual Cecropin, 0.03%)/mouse, Group C was administered the same low dose on each of Days 5, 6 and 7 and Group D administered the 0.35 mg/mouse of the control (cecropin minus) yeast on Days 5, 6 and 7. These doses were determined by calculating how much cecropin yeast was available for 20 doses and then matching that amount with an equal weight control (FIG. 7).

The mice in Group A became notably ill on Day 8 and the experiment was ended on Day 9 because of concerns about the cohort's health. The Y axis of FIG. 7 indicates the degree of parasitemia (parasites per 100 RBCs). Data from a single mouse in Group A was excluded because the mouse initially showed a small number of parasites in the peripheral blood, however the infection did not progress. This occurs occasionally.

In summary, the mice developed a notable parasitemia in the time frame that was expected and the results within each group had the amount of scatter that is typical of such infections.

However, malarial infections cause illness in animals through the release of a toxin. Any treatments that concurrently reduce the health status of animals will accelerate the infection and lead to a higher parasitemia at an earlier stage. Therefore trials such as this represent a balance of host damage (higher parasitemias) and parasite suppression (lower parasitemias). The animals that received infusions of both the low dose and the control appeared to have slight inflammation of the peritoneum. This may be due to either the presence of a yeast product that triggered innate immunity, or it is possible that, if the yeast is part of the normal flora of mice, the mice have some pre-existing immunity to the yeast extract. The mice in Groups C & D also seemed "less well" on Day 9. However this was a subjective measurement that frequently does not correlate with parasitemia. Thus, a better measure of general health is weight loss.

In Vivo Trial 3:

To Evaluate the Effect of Administering Yeast Expressing a Modified Form of the Naturally Occurring Protein Cecropin Administered by Injection at Three Time Points.

In this trial, mice were injected with cecropin yeast at three different time points concurrently with the initiation of infection.

Infection was initiated using the standard protocol which would be expected to show the first clinical signs on Day 5. Cecropin yeast was administered on Days 1, 2, 3, and 4. The low dose treatment was given at 200 µg per day (total 800 µg) and the high dose at 1 mg per day (total 4 mg). The control yeast (not expressing cecropin) was administered at 1 mg per day. A further group of mice was left untreated with any form of administration.

Figure 8:
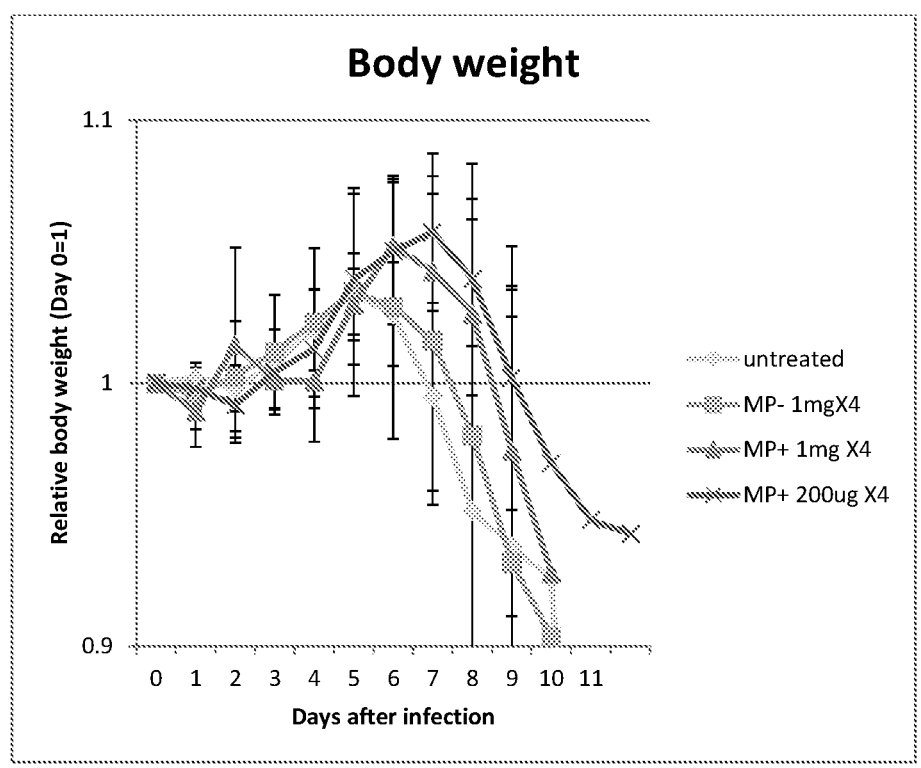
FIG. 8 shows relative weight of mice with high and low doses of yeast expressing modified cecropin administered to mice on days 1-4 post infection.
Figure 9:
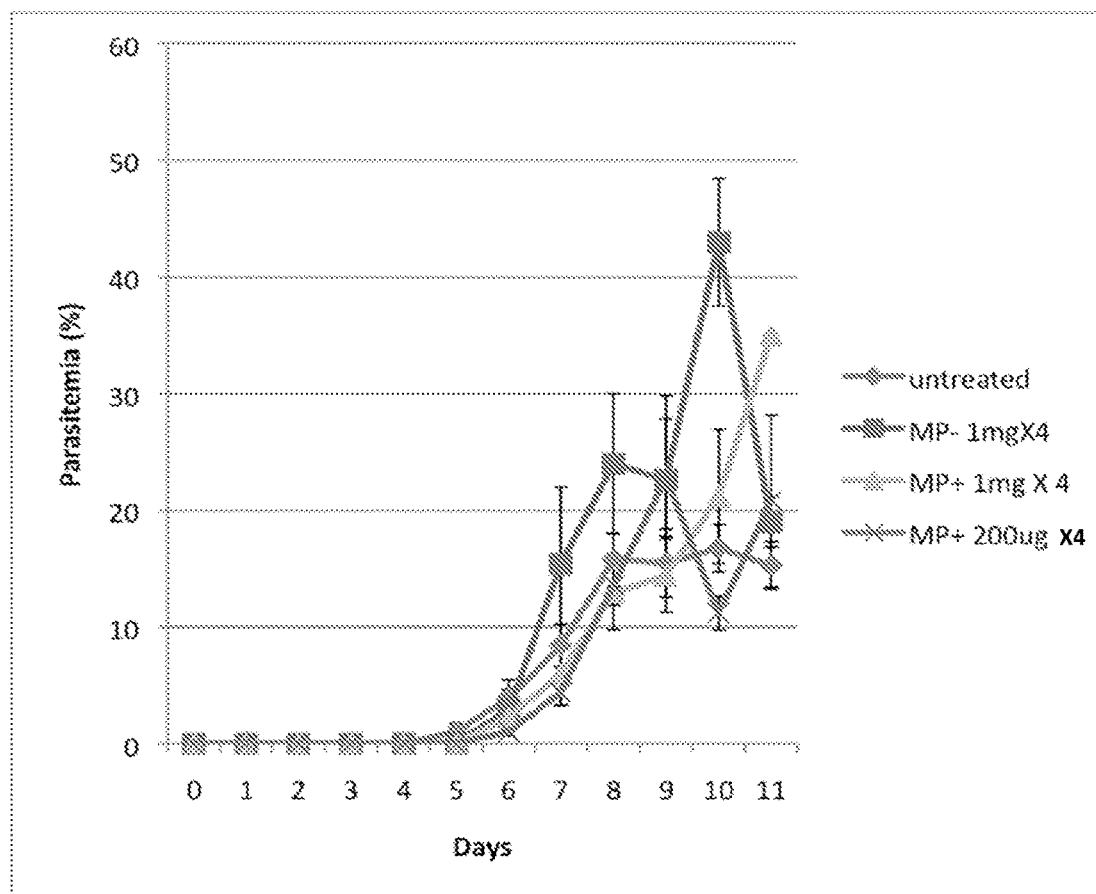
FIG. 9 shows the onset and pattern of parasitemia in untreated, control, low and high dose groups).
Figure 10:
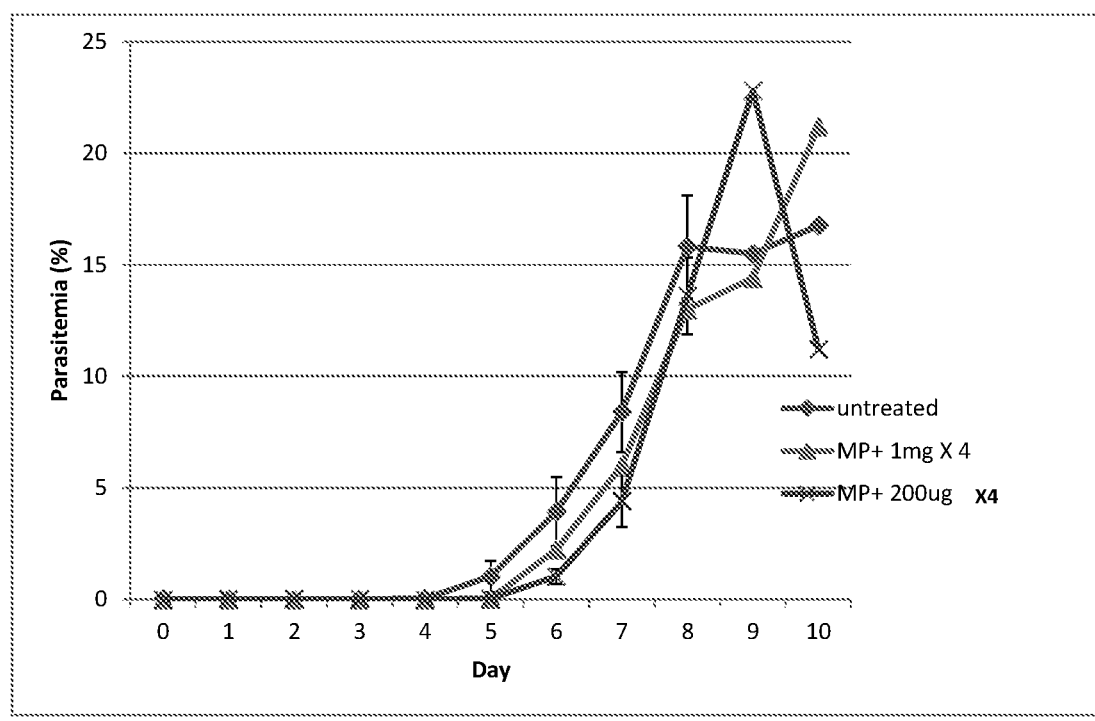
FIG. 10 shows onset and pattern of parasitemia in untreated, low and high dose groups.

The parameters measured were body weight (FIG. 8), parasitemia (FIGS. 9 and 10), and a subjective appraisal of general health.

In terms of general health, the untreated and control yeast groups displayed signs of malaria a day or two before the cecropin treated groups. The group receiving 1 mg cecropin per day appeared slightly healthier than the controls. By contrast the group receiving the low dose (200 ug per day) was noticeably healthier than any other group for the last two days. These observations, although subjective, were carried out 'blind' on unmarked groups.

Inhibiting E. coli Activity:

E. coli cells were grown overnight in LB broth at 37° C. Cells were serially diluted by up to $10^6$ cells/mL in water and split into 1 mL aliquots. The aliquots were split into three groups; Control, MP and Positive control. The control group was treated with 20 ug of total soluble protein extracted from the wild type CC11 yeast strain. The MP group was treated with 20 ug of total soluble protein extracted from a modified strain of yeast that expressed the modified anti-microbial peptide. The positive control group was treated with 50 ng of Ampicillin. Briefly, the treatments were added to the diluted cells and mixed thoroughly. The cells-protein mixtures were allowed to incubate for 20 min at 37° C. 100 uL from each tube was spread on LB agar plate and incubated overnight at 37° C. The next day colonies on each plate were counted and averaged (FIG. 11).

Other Hydrophilic Tails

Modified cecropins with hydrophilic tails ranging from 3 amino acids to 24 amino acids were synthesized, such as the modified cecropins listed in Tables 3-5. It was found that it was not possible to incorporate into the gene fragment bases encoding a tail length of 32 amino acids. The genes were synthesized commercially, cloned and expressed in the yeast and each clone was tested using the in vitro efficacy protocol to show efficacy against an endoparasite and/or bacteria.

In Vitro Efficacy in Parasites.

The parasite, P. falciparum, was shown to be killed by exposure to modified cecropins in vitro using an LDH assay that is specific for parasite LDH enzyme by the substitution of APAD for NAD. The presence of LDH activity distinguishes between live and dead Plasmodia. From these data a calculation was made of the concentration of protein (µg) in the samples that kills 50% of the parasites ($IC_{50}$); the stronger the anti-parasitic activity, the lower the dose required to achieve 50% kill. As described above, for in vitro testing against endoparasites, the material was serially diluted in a 96 well plate and as a control the last column on the plate did not have any test material added (i.e. it was just yeast lysate). A constant number of parasites was then added to each well and cultures were allowed to grow for 48 hours. The viability of the parasites was then determined by assaying for parasite specific LDH activity, or alternatively quantifying the amount of DNA in each well using SYBR Green I. The data was then analyzed by a computer-fit program to determine the $IC_{50}$ value for the material.

Figure 14:
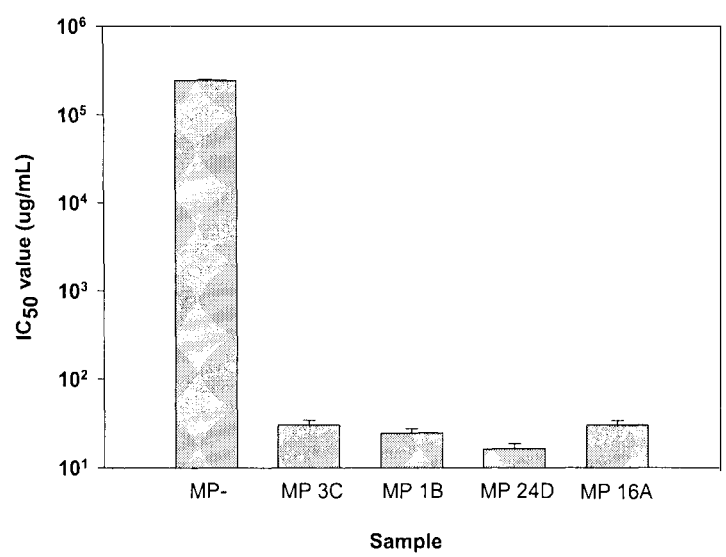
FIG. 14 shows the IC50 values for lethality of *Plasmodium falciparum* by yeast expressing modified cecropins having varying carboxy terminal tail lengths. MP−: negative control (yeast lysate). MP3: modified cecropin having a 3 amino acid tail, MP8: modified cecropin having an 8 amino acid tail, MP16: modified cecropin having a 16 amino acid tail, MP24: modified cecropin having a 24 amino acid tail.

The IC50 values for each of the modified cecropin peptides is provided in FIG. 14 and in the table below:

| Test Item | IC$_{50}$ µg lysate/mL |
|---|---|
| Control | 242.612 |
| 3 aa | 0.030 |
| 8 aa | 0.024 |
| 16 aa | 0.016 |
| 24 aa | 0.030 |

Compared with the Control value each of the test items showed a marked efficacy against the *Plasmodium* parasite evidenced by a significantly lower IC$_{50}$ value in each case. There was no significant difference between the differing tail lengths.

In Vitro Efficacy in Bacteria.

For in vitro testing against bacteria, *E. coli* cells are grown overnight in LB broth at 37° C. Cells are serially diluted by up to 10$^6$ cells/mL in water and split into 1 mL aliquots. The aliquots are then split into three groups; Control, MP and Positive control. The control group is treated with 20 ug of total soluble protein extracted from the wild type CC11 yeast strain. The MP group is treated with 20 ug of total soluble protein extracted from a modified strain of yeast that expresses the putative anti-microbial peptide. The positive control group is then treated with 5 ng of Ampicillin. Briefly, the treatments are to the diluted cells and mixed thoroughly. The cells-protein mixtures are allowed to incubate for 20 min at 37° C. 100 uL from each tube are then spread on LB agar plate and incubated overnight at 37° C. The next day colonies on each plate are counted and averaged.

Modified cecropins identified as having anti-bacterial activity are then tested for in vivo efficacy as disclosed herein.

In Vivo Trial 4:

MP− and MP+ Whole Yeast Cells were Administered Orally (Oral Gavage) to Mmice at a Dose of 500 µg/Mouse Every Day for 13 Days and the Parasitaemia Counted.

This experiment examined the effect on the outcome of a murine malaria (*Plasmodium berghei*) infection of administering mice orally (by gavage) yeast cells containing protein modified by the addition of an 8 amino acid, hydrophilic tail (MP). The mice were divided into 2 groups each of 8 mice. The mice were injected with 10$^6$ parasites i.p. according to the standard protocol for infection. Group A (Control group) was administered yeast samples that did not contain modified cecropin (MP−) in order to determine the influence of yeast cells alone on the outcome of the infection. Group B mice were treated with yeast cell (MP+) containing expressed cecropin from 1 day prior to infection to 13 days after the infection. The purpose of this group was to determine the influence of continued dosing of MP on the outcome of a normal infection.

Figure 15:
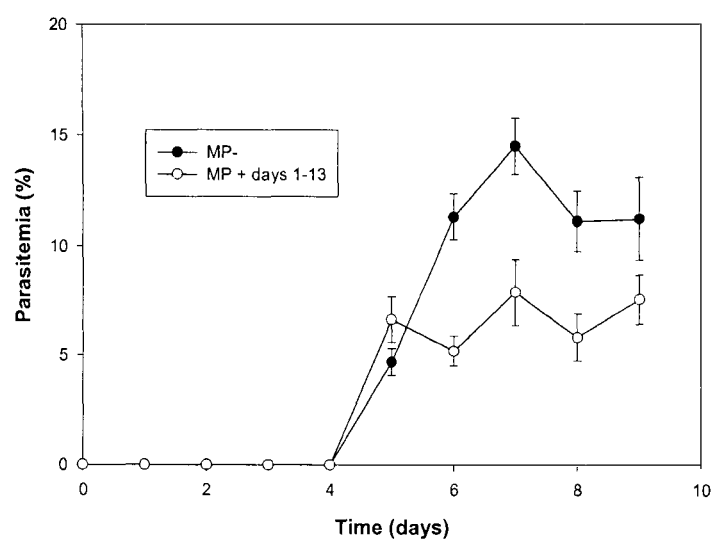
FIG. 15 shows the effect of whole yeast containing MP and whole yeast, without MP, administered orally. The mice treated with cecropin (MP+) were healthy throughout the trials and there was a significant difference between them and the controls in terms of parasite count.

The treated mice were healthy throughout the trial and there was a significant difference between them and the Controls in terms of parasite count as shown in the graph (FIG. 15).

While the present disclosure has been described with reference to what are presently considered to be the examples, it is to be understood that the disclosure is not limited to the disclosed examples. To the contrary, the disclosure is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

TABLE 1

Nucleotide sequence of the modified cecropin gene after optimization (SEQ ID NO: 1)

```
  1 atgaacttta cgaagctgtt cattctggtg gcgatcgctg
    tgctggtgat cgccggcatc 61 cagccggccg atgctgcacc aaggtggaaa ttcggcaaac
    gacttgaaag gctgggtcgg 121 aatgtgttca aggcggccaa aaaagcactg ccagtcatcg
    ccgggtacaa ggccctcgga 181 GAC CCA AAA GAC GAT GAC GCT AAG taa
```

TABLE 2

Amino acid sequence with tail (SEQ ID NO: 2)

MNFTKLFILVAIAVLVIAGIQPADAAPRWKFGKRLE

RLGRNVFKAAKKALPVIAGYKALG DPKDDDAK*

TABLE 3

Nucleic acid and amino acid sequence of modified cecropin with 16 amino acid tail:

Nucleic acid:
atgaacttta cgaagctgtt cattctggtg gcgatcgctg
tgctggtgat cgccggcatc cagccggccg atgctgcacc
aaggtggaaa ttcggcaaac gacttgaaag gctgggtcgg
aatgtgttca aggcggccaa aaaagcactg ccagtcatcg
ccgggtacaa ggccctcgga **GAC CCA AAA GAC GAT
GAC GCT AAG GAC CCA AAA GAC GAT GAC GCT AAG
TAA** (SEQ ID NO: 5)

Amino acid
MNFTKLFILVAIAVLVIAGIQPADAAPRWKFGKRLE
RLGRNVFKAAKKALPVIAGYKALG DPKDDDAK DPKDDDAK*
(SEQ ID NO: 6)

TABLE 4

Nucleic acid and amino acid sequence of modified cecropin with 24 amino acid tail:

Nucleic acid:
atgaacttta cgaagctgtt cattctggtg gcgatcgctg
tgctggtgat cgccggcatc cagccggccg atgctgcacc
aaggtggaaa ttcggcaaac gacttgaaag gctgggtcgg
aatgtgttca aggcggccaa aaaagcactg ccagtcatcg
ccgggtacaa ggccctcgga **GAC CCA AAA GAC GAT
GAC GCT AAG GAC CCA AAA GAC GAT GAC GCT AAG
GAC CCA AAA GAC GAT GAC GCT AAG** TAA (SEQ ID NO: 7)

Amino acid
MNFTKLFILVAIAVLVIAGIQPADAAPRWKFGKRLE
RLGRNVFKAAKKALPVIAGYKALG
DPKDDDAK DPKDDDAK DPKDDDAK* (SEQ ID NO: 8)

TABLE 5

Nucleic acid and amino acid sequence of
modified cecropin with a 3 amino acid tail:

Nucleic acid:
atgaacttta cgaagctgtt cattctggtg gcgatcgctg
tgctggtgat cgccggcatc cagccggccg atgctgcacc
aaggtggaaa ttcggcaaac gacttgaaag gctgggtcgg
aatgtgttca aggcggccaa aaaagcactg ccagtcatcg
ccgggtacaa ggccctcgga GAC CCA AAA taa
(SEQ ID NO: 9)

Amino acid
MNFTKLFILVAIAVLVIAGIQPADAAPRWKFGKRLE
RLGRNVFKAAKKALPVIAGYKALG DPK* (SEQ ID NO: 10)

TABLE 6

Nucleic acid and amino acid sequence of
modified cecropin with 32 amino acid tail:

Nucleic acid:
atgaacttta cgaagctgtt cattctggtg gcgatcgctg
tgctggtgat cgccggcatc cagccggccg atgctgcacc
aaggtggaaa ttcggcaaac gacttgaaag gctgggtcgg
aatgtgttca aggcggccaa aaaagcactg ccagtcatcg
ccgggtacaa ggccctcgga **GAC CCA AAA GAC GAT
GAC GCT AAG GAC CCA AAA GAC GAT GAC GCT AAG
GAC CCA AAA GAC GAT GAC GCT AAG GAC CCA
AAA GAC GAT GAC GCT AAG TAA** (SEQ ID NO: 11)

Amino acid
MNFTKLFILVAIAVLVIAGIQPADAAPRWKFGKRLE
RLGRNVFKAAKKALPVIAGYKALG **DPKDDDAK DPKDDDAK
DPKDDDAK DPKDDDAK*** (SEQ ID NO: 12)

REFERENCES

Bouharoun-Tayoun H, Attanath P, Sabcharoen A, Chong-suphajaisiddhi T, Druilhe P (1990) Antibodies that protect humans against *Plasmodium falciparum* blood stages do not on their own inhibit parasite growth and invasion in vitro but act in cooperation with monocytes. J Exp Med 172: 1633-1641.

Beier, J. C. (1998) Malaria parasite Development in mosquitoes. Ann Rev Entomol 43:519-543.

Boman, H. G. 1991. Antibacterial peptides: key components needed in immunity. Cell 65:205-207.

Boman, H. G., L Faye, H. Gudmundsson, J.-Y. Lee, and D.-A. Lidholm. 1991. Cell-free immunity in Cecropia. A model system for antibacterial proteins. Eur. J. Biochem. 201:23-31.

Bradbury, A. F. and Smyth, D. G. 91991) Peptide amidation. Trends Biochem. Sci. 16:112-115.

Callaway, J. E., Lai, J., Haselbeck, B., Baltaian, M., Bonnesen, S. P., Weickmann, J., Wilcox, G. and Lei, S. P. (1993) Modification of the C-terminus of cecropin is essential for broad-spectrum antimicrobial activity. Antimicrob. Agents Chemother. 37:1614-1619.

Chopra, L 1993. The magainins: antimicrobial peptides with potential for topical application. J. Antimicrob. Chemother. 32: 351-353.

Casteels, P., C. Ampe, F. Jacobs, M. Vaeck, and P. Tempst. 1989. Apidaecins: antibacterial peptides from honeybees. EMBO J. 8:2387-2391.

Chalk, R., Townson, H., Natori, S., Desmond, H. and Ham, P. J. (1994) Purification of an insect defensin from the mosquito, *Aedes aegypti*. Insect Biochem Mol Biol 24: 403-410.

Cho, W. L., Fu, Y. C., Chen, C. C. and Ho, C. M. (1996) Cloning and characterization of cDNAs encoding the antibacterial peptide, defensin A, from the mosquito, *Aedes aegypti*. Insect. Biochem Mol Biol 26: 395-402.

Cohen S, McGregor I A, Carrington S (1961) Gamma-globulin and acquired immunity to human malaria. Nature 192: 733-737.

Casteels, P., C. Ampe, F. Jacobs, M. Vaeck, and P. Tempst. 1989. Apidaecins: antibacterial peptides from honeybees. EMBO J. 8:2387-2391.

Christensen, B., J. Fink, R. B. Merrifield, and D. Mauzerall. 1988. Channel-forming properties of cecropins and related model compounds incorporated into planar lipid membranes. Proc. Natl. Acad. Sci. USA 85:5072-5076.

Dimopoulos, G., Seeley, D., Wolf, A. and Kafatos, F. C. (1998) Malaria infection of the mosquito *Anopheles gambiae* activates immune-responsive genes during critical stages of the parasite life cycle. EMBO J. 17: 6115-6123.

Diamond, G., M. Zasloff, H. Eck, M. Bressaur, W. L. Maloy, and C. L Bevins. 1991. Tracheal antimicrobial peptide, a novel cysteine-rich peptide from mammalian tracheal mucosa: peptide isolation and cloning of a cDNA. Proc. Natl. Acad. Sci. USA 88:3952-3956.

Durell, S. R., G. Raghunathan, and H. R Guy. 1992. Modeling the ion channel structure of cecropin. Biophys. J. 63:1623-1631.

Dauvillée D, Delhaye S, Gruyer S, Slomianny C, Moretz S E, et al. (2010) Engineering the Chloroplast Targeted Malarial Vaccine Antigens in *Chlamydomonas* Starch Granules. PLoS ONE 5(12): e15424. doi:10.1371/journal.pone.0015424

Dauville'e D, Chochois V, Steup M, Haebel S, Eckermann N, et al. (2006) Plastidial phosphorylase is required for normal starch synthesis in *Chlamydomonas reinhardtii*. Plant Journal 48: 274-285.

Eric Calvo, Van M Pham, Osvaldo Marinotti, John F Andersen and José M C Ribeiro. The salivary gland transcriptome of the neotropical malaria vector *Anopheles darlingi* reveals accelerated evolution of genes relevant to Hematophagy. BMC Genomics 2009, 10:57 doi:10.1186/1471-2164-10-57

Ganz T. Lehrer R I. Antimicrobial peptides of vertebrates. Curr. Opin. Immunol. 1998 10:41-4.

Gietz, R. D. and R. A. Woods. (2002) Transformation of Yeast by the Liac/SS Carrier DNA/PEG Method. Methods in Enzymology 350: 87-96.

Guerra C A, Gikandi P W, Tatem A J, Noor A M, Smith D L, et al. (2008) The limits and intensity of *Plasmodium falciparum* transmission: implications for malaria control and elimination worldwide. PLos Med 5: 38.

Good M F (2001) Towards a blood-stage vaccine for malaria: are we following all the leads. Nat Rev Immunol 1: 117-125.

Guiliani, A; Pirri, G; Nicoletto, S (March 2007) 'Antimicrobial peptides: an overview of a promising class of therapeutics" Cent. Eur. J. Biol 2 (1): 1-33, doi: 10.2478/s 1135-007-0010-5.

Hara, S., Taniai, K., Kato, Y. and Yamakawa, M. (1994) Isolation and a-amidation of the non-amidated from for cecropin D from larvae of *Bombyx mori*. Comp. Biochem. Physiol. 108:303-308.

Hay S I, Guerra C A, Gething P W, Patil A P, Tatem A J, et al. (2009) A world malaria map: *Plasmodium falciparum* endemicity in 2007. PLoS Med 6: e1000048.

Hetru, C., Hoffmann, D and Bulet, P (1998) Antimicrobial peptides from Insects. In molecular mechanism of Immune Responses in Insects (Brey, P. T and Hultmark, D., eds) pp 40-66, Chapman & Hall London.

Hoffmann, J. A., Reichhart, J. M and hetru, C (1996) Innate immunity in higher insects. Curr Opin Immunol 8: 8-13.

Hoop T P and Woods K R (1981) Prediction of protein antigenic determinants from amino acid sequences. Proc Natl Acad Sci USA 78:3824.

JAYNES, J. M.; BURTON, C. A.; BARR, S. B.; JEFFERS, G. W.; JULIAN, G. R.; WHITE, K. L.; ENRIGHT, F. M.; KLEI, T R.; LAINE, R. A. In vitro cytocidal effect of novel lytic peptides on *Plasmodium falciparum* and *Trypanosoma cruzi*. FASEB J 2: 2878-2883; 1988.

Khmelnitsky, Y. L., Belova, A. B., Levashov, A. V. and Mozhaev, V. V. (1991) Relationship between surface hydrophilicity of a protein and its stability against denaturation by organic solvents. FEBS Lett. 284(2):267-9.

Lehrer, R I., T. Ganz, and M. E. Selsted. 1991. Defensins: endogenous antibiotic peptides of animal cells. Cell 64:229-230.

Li, Z. Q., Merrifiled, R. B., Boman, I. A., and Boman, H. G. (1988) Effects on electrophoretic mobility and antimicrobial spectrum of removal of two residues from synthetic sarcotoxin IA and addition of the same residues to cecropin B. FEBS Lett. 231:299-302.

Lowenberger, C., Bulet, P., Charlet, M., Hetru, C., Hodgeman, B., Christensen, B. M. and Hoffmann, J. A. (1995) Insect immunity: isolation of three novel inducible antibacterial defensins from the vector mosquito, *Aedes aegypti*. Insect Biochem Mol Biol 25: 867-873.

Malkin E, Long C A, Stowers A W, Zou L, Singh S, et al. (2007) Phase 1 study of two merozoite surface protein 1 (MSP 1 (42) vaccines for *Plasmodium falciparum* malaria. Plos Clin Trials 2: e12.

Nakamura, T., H. Furunaka, T. Miyata, F. Tokunaga, T. Muta, S. Iwanaga, M. Niwa, T. Takao, and Y. Shimonishi. 1988. Tachyplesin, a class of antimicrobial peptides from the hemocytes of the horseshoe crab (*Tachypleus tridentatus*). J. Biol. Chem. 263:16709-16713.

Philip Bejon, George Warimwe, Claire L. Mackintosh, Margaret J. Mackinnon, Sam M. Kinyanjui, Jennifer N. Musyoki, Peter C. Bull, and Kevin Marsh. Analysis of Immunity to Febrile Malaria in Children That Distinguishes Immunity from Lack of Exposure, *Infect. Immun.* 77 (5) 1917-1923 May 2009.

Parra-Lopez, C., M. T. Baer, and E. A. Groisman. 1993. Molecular genetic analysis of a locus required for resistance to antimicrobial peptides in *Salmonella typhimurium*. EMBO J. 12:4053-4062.

Richman, A. and Kafatos, F. C. (1996) Immunity to eukaryotic parasites in vector insects. Curr Opin Immunol 8: 14-19.

Richman, A. M., Dimopoulos, G., Seeley, D. and Kafatos, F. C. (1997) *Plasmodium* activates the innate immune response of *Anopheles gambiae* mosquitoes. EMBO J. 16: 6114-6119.

Shahabuddin, M., Fields, I., Bulet, P., Hoffmann, J. A. and Miller, L. H. (1998) *Plasmodium gallinaceum*: differential killing of some mosquito stages of the parasite by insect defensin. Exp Parasitol 89: 103-112.

Sabchareon A, Burnouf T, Ouattara D, Attanath P, Bouharoun-Tayoun H, et al. (1991) Parasitologic and clinical human response to immunoglobulin administration in falciparum malaria. Am J Trop Med Hyg 45: 297-308.

Snow R W, Guerra C A, Noor A M, Myint H Y, Hay S I. The global distribution of clinical episodes of *Plasmodium falciparum* malaria. Nature 434: 214-217.

Sturm A, Amino R, van de Sand C, Regen T, Retzlaff S, et al. (2006) Manipulation of host hepatocytes by the malaria parasite for delivery into liver sinusoids. Science 313: 1245-1246.

Wade, D., A. Boman, B. WAhlin, C. M. Drain, D. Andreu, H. G. Boman, and R. B. Merrifield. 1990. All-D amino acid-containing channel-forming antibiotic peptides. Proc. Natl. Acad. Sci. USA 87:4761-4765.

WHO, World malaria report, 2008. Available: http://apps.who.int/malaria/wnr2008/malaria2008.pdf.

Warburg, A. and Miller, L. H. (1991) critical stages in the development of *Plasmodium* in mosquitoes. Parasitology Today 7: 179-181.

Zaslof, M. 1987. Magainins, a class of antimicrobial peptides from *Xenopus* skin: isolation, characterization of two active forms, and partial cDNA sequence of a precursor. Proc. Natl. Acad. Sci. USA 84:5449-5453.

Zasloff, M., B. Martin, and H.-C. Chen. 1988. Antimicrobial activity of synthetic magainin peptides and several analogues. Proc. Natl. Acad. Sci. USA 85:910-913.

The invention claimed is:

1. A method of inhibiting an organism selected from the group consisting of an endoparasite, a bacterium and a malarial parasite, comprising administering a modified cecropin, wherein the modified cecropin comprises a peptide fused to a hydrophilic tail lacking a C-terminal glycine, peptide is selected from the group consisting of a cecropin, a variant peptide having at least 90% sequence identity with a cecropin, and a variant peptide having at least 95% sequence identity with a cecropin.

2. The method of claim 1, wherein the organism is an endoparasite.

3. The method of claim 1, wherein the organism is a bacterium.

4. The method of claim 1, wherein the hydrophilic tail comprises 3-24 amino acids.

5. The method of claim 1, wherein the hydrophilic tail comprises 8-16 amino acids.

6. The method of claim 1, wherein the peptide is a cecropin.

7. The method of claim 1, wherein the modified cecropin comprises a sequence selected from the group consisting of SEQ ID NO: 2, SEQ ID NO: 6, SEQ ID NO: 8, SEQ ID NO: 10 and a variant thereof, wherein the variant is a sequence having at least 90% sequence identity with a sequence selected from the group consisting of SEQ ID NO: 2, SEQ ID NO: 6, SEQ ID NO: 8 and SEQ ID NO: 10.

8. The method of claim 2, wherein the endoparasite is a malarial parasite.

9. The method of claim 3, wherein the bacterium is *E. coli*.

10. The method of claim 3, wherein the bacterium is *Pseudomonas*.

11. The method of claim 6, wherein the cecropin is cecropin B.

12. The method of claim 6, wherein the hydrophilic tail comprises 3-24 amino acids.

13. The method of claim 6, wherein the hydrophilic tail comprises 8-16 amino acids.

14. The method of claim 6, wherein the organism is an endoparasite.

15. The method of claim 14, wherein the endoparasite is a malarial parasite.

16. The method of claim 6, wherein the organism is a bacterium.

17. The method of claim 16, wherein the bacterium is *Pseudomonas*.

18. The method of claim 16, wherein the bacterium is *E. coli*.

19. The method of claim 7, wherein the sequence is SEQ ID NO: 2 or SEQ ID NO: 6.

20. The method of claim 7, wherein the sequence is SEQ ID NO: 8 or SEQ ID NO: 10.

* * * * *